(12) United States Patent
Hebb et al.

(10) Patent No.: US 11,167,133 B2
(45) Date of Patent: Nov. 9, 2021

(54) INTRATUMORAL MODULATION THERAPY

(71) Applicant: LONDON HEALTH SCIENCES CENTRE RESEARCH INC., London (CA)

(72) Inventors: Matthew Olding Hebb, London (CA); Susanne Schmid, London (CA)

(73) Assignee: LONDON HEALTH SCIENCES CENTRE RESEARCH INC., London (CA)

(*) Notice: Subject to any disclaimer, the term of this patent is extended or adjusted under 35 U.S.C. 154(b) by 17 days.

(21) Appl. No.: 15/574,014

(22) PCT Filed: May 16, 2016

(86) PCT No.: PCT/CA2016/050556
§ 371 (c)(1),
(2) Date: Nov. 14, 2017

(87) PCT Pub. No.: WO2016/179712
PCT Pub. Date: Nov. 17, 2016

(65) Prior Publication Data
US 2018/0289954 A1    Oct. 11, 2018

Related U.S. Application Data

(60) Provisional application No. 62/161,481, filed on May 14, 2015.

(51) Int. Cl.
*A61N 1/30*    (2006.01)
*A61N 1/36*    (2006.01)
(Continued)

(52) U.S. Cl.
CPC .............. *A61N 1/306* (2013.01); *A61K 41/00* (2013.01); *A61N 1/327* (2013.01);
(Continued)

(58) Field of Classification Search
CPC .... A61N 1/306; A61N 1/36002; A61N 1/327; A61N 1/205; A61N 1/0529; A61N 1/06; A61K 41/00; C12N 13/00
See application file for complete search history.

(56) References Cited

U.S. PATENT DOCUMENTS 5,529,574 A * 6/1996 Frackelton ............... A61N 1/05
604/22
2004/0010290 A1 * 1/2004 Schroeppel ............ A61N 1/205
607/3

(Continued)

OTHER PUBLICATIONS

Cucullo et al., Very Low Intensity Alternating Current Decreases Cell Proliferation, (2005), GLIA 51:65-72, pp. 65-72 (Year: 2005).*

(Continued)

*Primary Examiner* — Catherine M Voorhees
(74) *Attorney, Agent, or Firm* — Eduardo Krupnik

(57) ABSTRACT

An intratumoral modulation therapy (IMT) method for the treatment of nervous system and systemic tumor in a patient which includes: (a) chronically implanting an electrode adjacent to or in the tumor of the patient or in a residual tumor bed, the electrode having electrical leads connected thereto; and (b) generating electric stimulation and applying the electric stimulation through the electrical leads to the electrode adjacent to or within the tumor. A method of transferring genetic material to a tumor cell which includes: (a) positioning an electrode adjacent to the tumor cell, the electrode having electrical leads connected thereto; (b) generating electric stimulation and applying the electric stimulation through the electrical leads to the electrode adjacent the cancer cell; and (c) delivering the genetic material to the tumor cell treated with the continuous alternating electric stimulation.

22 Claims, 19 Drawing Sheets

(51) Int. Cl.
    *A61N 1/32*     (2006.01)
    *A61K 41/00*     (2020.01)
    *A61N 1/06*     (2006.01)
    *A61N 1/05*     (2006.01)
    *C12N 13/00*     (2006.01)
    *A61N 1/20*     (2006.01)

(52) U.S. Cl.
    CPC ........ *A61N 1/36002* (2017.08); *A61N 1/0529* (2013.01); *A61N 1/06* (2013.01); *A61N 1/205* (2013.01); *C12N 13/00* (2013.01)

(56) References Cited

U.S. PATENT DOCUMENTS

| | | |
|---|---|---|
| 2004/0254618 A1 | 12/2004 | Sinsheimer et al. |
| 2005/0222623 A1* | 10/2005 | Kroll ............ A61N 1/326 607/2 |
| 2014/0039489 A1* | 2/2014 | Davalos ............ A61N 1/327 606/34 |

OTHER PUBLICATIONS

Cavenee, WK, et al. WHO Classification of Tumours of the Central Nervous System. WHO Pulblications Fourth edition, 2007.

Orlowski, S., et al. Transient electropermeabilization of cells in culture. Increase of the cytotoxicity of anticancer drugs. Biochem. Pharmacol. 37:4727-4733; 1988.

Zimmermann, U. Electric field-mediated fusion and related electrical phenomena.Biochim Biophys Acta. Nov. 30, 1982;694(3):227-77.

Horikoshi, T, et al. Enhancing effect of electric stimulation on cytotoxicity of anticancer agents against rat and human glioma cells.Brain Res Bull. Mar. 15, 2000;51(5):371-8.

Salford, LG, et al. A new brain tumour therapy combining bleomycin with in vivo electropermeabilization. Biochem Biophys Res Commun. Jul. 30, 1993;194(2):938-43.

Pudenz, R. Adverse effects of electrical energy applied to the nervous system. Neurosurgery 1:190-191; 1977.

Kirson, Ed, et al. Alternating electric fields arrest cell proliferation in animal tumor models and human brain tumors. Proc Natl Acad Sci U S A. Jun. 12, 2007;104(24):10152-7. Epub Jun. 5, 2007.

Pless, M, et al.Tumor treating fields: concept, evidence and future. Expert Opin Investig Drugs. Aug. 2011;20(8):1099-106. doi: 10.1517/13543784.2011.583236. Epub May 9, 2011.

Stupp, R, et al.NovoTTF-100A versus physician's choice chemotherapy in recurrent glioblastoma: A randomised phase III trial of a novel treatment modality. Eur J Cancer. Sep. 2012;48(14):2192-202. Epub May 18, 2012.

Kanner, AA, et al., on behalf of EF-11 Investigators. Post Hoc analyses of intention-to-treat population in phase III comparison of NovoTTF-100A™ system versus best physician's choice chemotherapy. Semin Oncol. Oct. 2014;41 Suppl 6:S25-34.

Deniau JM, et al. Deep brain stimulation mechanisms: beyond the concept of local functional inhibition. Eur J Neurosci. Oct. 2010;32(7):1080-91. doi: 10.1111/j.1460-9568.2010.07413.x.

Wang, J, et al. Delivery of siRNA therapeutics: barriers and carriers. Aaps J. Dec. 2010;12(4):492-503.

Mossop, BJ, et al. Electric fields in tumors exposed to external voltage sources: implication for electric field-mediated drug and gene delivery. Ann Biomed Eng. Oct. 2006;34(10):1564-72.

Tang, L, et al. Apoptosis induction with electric pulses—a new approach to cancer therapy with drug free. Biochem Biophys Res Commun. Dec. 25, 2009;390(4):1098-101.

Acunzo J, et al. Hsp27 as a therapeutic target in cancers. Curr Drug Targets. Apr. 2014;15(4):423-31.

Lianos, GD, et al. The role of heat shock proteins in cancer. Cancer Lett. May 1, 2015;360(2):114-8.

Yang, I, et al. Heat shock proteins in glioblastomas. Neurosurg Clin N Am. Jan. 2010;21(1):111-23.

Belkacemi, L, Hebb, MO. HSP27 knockdown produces synergistic induction of apoptosis by HSP90 and kinase inhibitors in glioblastoma multiforme. Anticancer Res. Sep. 2014;34(9):4915-27.

Aloy, MT, et al. Protective role of Hsp27 protein against gamma radiation-induced apoptosis and radiosensitization effects of Hsp27 gene silencing in different human tumor cells. Int J Radiat Oncol Biol Phys. Feb. 1, 2008;70(2):543-53.

Jakubowicz-Gil, J, et al. Silencing of Hsp27 and Hsp72 in glioma cells as a tool for programmed cell death induction upon temozolomide and quercetin treatment. Toxicol Appl Pharmacol. Dec. 15, 2013;273(3):580-9.

Mathieu, D, et al. Standardization and detailed characterization of the syngeneic Fischer/F98 glioma model. Can J Neurol Sci. Aug. 2007;34(3):296-306.

Beaman, GM, et al. Reliability of HSP70 (HSPA) expression as a prognostic marker in glioma. Mol Cell Biochem. Aug. 2014;393(1-2):301-7.

Wang, X, et al. HSP27, 70 and 90, anti-apoptotic proteins, in clinical cancer therapy (Review). Int J Oncol. Jul. 2014;45(1):18-30.

Ostermann, S., et al. Plasma and cerebrospinal fluid population pharmacokinetics of temozolomide in malignant glioma patients. Clin Cancer Res. Jun. 1, 2004;10(11):3728-36.

Zhou, Q, et al. Preclinical pharmacokinetic and pharmacodynamic evaluation of metronomic and conventional temozolomide dosing regimens. J Pharmacol Exp Ther. Apr. 2007;321(1):265-75.

Gil, S, et al. Survival analysis of F98 glioma rat cells following minibeam or broad-beam synchrotron radiation therapy. Radiat Oncol. Apr. 13, 2011;6:37.

Bolcaen J, et al. (18)F-fluoromethylcholine (FCho), (18)Ffluoroethyltyrosine (FET), and (18)F-fluorodeoxyglucose (FDG) for the discrimination between highgrade glioma and radiation necrosis in rats: a PET study. Nucl Med Biol. Jan. 2015;42(1):38-45.

Lacouture, ME, et al. Characterization and management of dermatologic adverse events with the NovoTTF-100A System, a novel anti-mitotic electric field device for the treatment of recurrent glioblastoma. Semin Oncol. Jun. 2014;41 Suppl 4:S1-14. doi: 10.1053.

Stupp, R, et al. Maintenance Therapy With Tumor-Treating Fields Plus Temozolomide vs Temozolomide Alone for Glioblastoma: A Randomized Clinical Trial. JAMA. Dec. 15, 2015;314(23):2535-43. doi: 10.1001.

Garcia, PA, et al. Non-thermal irreversible electroporation (N-TIRE) and adjuvant fractionated radiotherapeutic multimodal therapy for intracranial malignant glioma in a canine patient. Technol Cancer Res Treat. Feb. 2011;10(1):73-83.

International Search Report and the Written Opinion of the International Searching Authority, for PCT/CA2016/050556.

Beebe, S. J., et al. "Bioelectric Applications for Treatment of Melanoma", Cancers, Sep. 2010, vol. 2, Issue 3, pp. 1731-1770.

Au, J.T., et al. "Irreversible Electroporation is a Surgical Ablation Technique That Enhances Gene Transfer", Surgery, Sep. 2011, vol. 150, Issue 3, pp. 474-479.

\* cited by examiner ly to disturb the dynamic equilibrium of the tumor cell, its surrounding normal cells, the organ where the tumor has taken root, and the entire organism. The object of such an electrical stimulation, according to '808, can be to cause cellular malfunction, leading to cellular death, which in turn leads to tumor shrinkage. '808 teaches away from use of electrotherapy to treat solid cancers as US 6,366,808, on page 3 beginning at line 48 states that attempts to treat cancers with currents have not been successful.

INTRATUMORAL MODULATION THERAPY

CROSS REFERENCE TO RELATED APPLICATIONS

This application is a national stage application under 35 U.S.C. 371 of International Application No. PCT/CA2016/050556, filed May 16, 2016, which in turn claims the benefit under 35 U.S.C. 119(e) of U.S. Provisional Ser. No. 62/161,481, filed May 14, 2015, the contents of each of which are hereby incorporated by reference into the present disclosure.

FIELD OF THE INVENTION

The present invention relates to intratumoral modulation therapy. More specifically, the present invention relates to the treatment of tumors and cancer by delivering in situ electrical stimulation.

BACKGROUND OF THE INVENTION

Glioblastoma (GBM) is the most common primary brain tumor in adults, with highly invasive cells that infiltrate multiple cerebral lobes, deep nuclei and across midline commissures. Standard of care entails maximal safe resection followed by chemoradiation and affords a median survival of 12-18 months (1). Surgery may be limited or not safely feasible when eloquent brain regions are involved, thus further reducing the duration of tumor control and patient survival. Various forms of electrotherapy have been tested for efficacy against systemic cancers, with less progress made in effective application for brain tumors, such as GBM.

Electroporation, for example, delivers short trains of high voltage pulses that produce nanoscale holes in the cell membrane. This effect facilitates uptake of chemotherapeutic agents or leads to metabolic instability and cell death. Four to eight pulses at a frequency of 1 Hz, intensity of 1000-1750 V/cm and pulse width of 0.1 msec produce marked cytotoxicity and enhance sensitivity to chemotherapy in GBM cells in vitro (2-4). In vivo studies showed that pulse trains of 400V delivered within the glioma mass, and combined with bleomycin, significantly prolonged animal survival (5). Unfortunately, the extreme stimulation intensities of electroporation pose significant limitations on its use in human GBM patients, particularly when the tumor is diffuse or in eloquent brain areas (6).

The use of alternating electric fields (AEFs) is another electrotherapeutic strategy that can decrease cell proliferation and viability in various cancers, including GBM. The biological action is frequency-dependent and anti-cancer effects may be achieved at rates between 10-1000 kHz, above which risks tissue heating and thermal injury (7, 8). AEFs interfere with charged intracellular molecules and thereby disrupt spindle microtubule organization, leading to ineffective cytokinesis and membrane rupture. Post-mitotic (i.e., non-neoplastic) neural cells in the brain are less impacted and AEFs appear to confer a degree of tumor selectivity. A portable, battery-powered device to deliver low intensity (1-2 V/cm) AEFs of 200 kHz across the patients' cranium is now a U.S. Food and Drug Administration (FDA)-approved treatment for individuals with recurrent GBM who have exhausted surgical and radiation treatments. A phase Ill clinical trial was conducted to compare AEFs (n=116) with physician-choice chemotherapy (n=113) in recurrent GBM (9). The AEFs are delivered using arrays of insulated electrodes that are adhered to the patients' shaved scalp and connected via multiple cables to a portable generator that is carried around with the individual. Dermatological complications, including allergic and irritant dermatitis, mechanical lesions, ulcers, and skin infection are common (28). Treatment cycles were 4 weeks in duration and uninterrupted therapy was recommended, with a 1 hour break twice per day. While there was no difference in the overall or progression-free survival between the groups, subgroup analysis indicated that AEFs may produce better outcomes, when groups are controlled for compliance and completion of the therapeutic regime (10). More recent data indicates that AEFs may also prolong the progression-free and overall survival when combined with TMZ (29). Patient compliance may also present a significant challenge in successful AEF application as adherence to therapy was the main predictor of improved overall survival, with patients who used the device for more than 18 hours a day living significantly longer than those who used it less. AEFs have no half-life and continuous application is required to maintain therapeutic effect. The reasons for compliance difficulties have not been defined but could relate to the operational aspects (e.g., requiring a shaved scalp, dermatological complications, perpetual application) and stigma of using an external treatment system. Treatment efficacy of these externally-applied AEFs may also be limited by an inability to conform field dimensions to maximize stimulation intensity and avoid off-target injury Deep brain stimulation (DBS; 100-300 Hz) is commonly used to treat movement disorders (e.g., Parkinson's disease) and delivered through an implantable lead and generator system. The technology entails implantation of multi-contact leads into target brain regions, with control via a remote-accessed pulse generator housed in the subcutaneous tissues of the chest. The impact of DBS in the brain is complex and has been widely studied. It is generally accepted that this intervention serves to modulate electrochemical communication within disease-affected circuitry and thereby disrupts pathogenic neural activity (11). Little is known about the therapeutic potential of DBS-type therapy in intracerebral tumors.

Garcia et al. (2011) describe initiation of electroporation in cells by exposing cells or tissues to electric fields. Garcia et al. deliver in vivo 500 V-625 V to a canine malignant glioma (30).

U.S. Pat. No. 6,528,315 describes methods for transferring in vivo nucleic acids into cells using electric fields of 1-600 V/cm, frequency 1 Hz. This patent document, however, does not teach that these electric fields may be used to kill tumor cells.

US Pat. Appl. Publ. No. 20050222646 describes the use of electrical therapy in the treatment of cancer. This patent application only describes the use of direct current (see examples 1, 2, 4 and 5). That is, US Pat. Appl. Publ. No. 20050222646 does not provide any parameters with regard to alternating current or electric fields. According to this patent application the method involves delivering between 3 to 25 volts of direct current to kill cancer cells. The effect on cell death, as defined only by voltage, will be highly variable depending upon the other parameters (frequency, pulse width, current etc). The effects will also be highly contextual as 'voltage' will be mitigated by hardware and biological factors that influence tissue/electrode resistance/impedance. This patent application does not teach what will universally work, particularly for neoplasms affecting the nervous system.

U.S. Pat. No. 6,366,808 ("'808") describes an implantable electrical method and apparatus for the treatment of solid tumors based on the usage of various electrical voltages to assist in specific ways to reduce tumor size. It describes the use of 20 mV-500 mV and 100 mV to 10 V of direct current to kill tumor cells. '808 does not disclose the use of alternating electrical stimulation and is silent about frequencies. Furthermore, '808 teaches duration between 1 minute and 1 month of treatment (i.e., not a perpetual or chronically sustained therapy), and the device description indicates that the mechanical stringency of the requirements for the hardware is therefore less than for e.g. pacemaker devices. '808 also teaches that the electrical therapy delivered by the source of electrical power also involves the application of between 1 and 10,000 voltage pulses. GBM, in particular, is highly recalcitrant to current therapies and so one would need to be prepared to deliver a more perpetual treatment to optimize remission time or obtain a cure. '808 is silent with respect to, and does not teach about, frequencies. In view of the foregoing, '808 does not teach or suggest the chronic treatment of cancer.

There is significant potential for the use of electrotherapy in brain/nervous system tumor management, including GBM management, however the technologies described above have significant disadvantages that limit clinical applicability and/or efficacy.

SUMMARY OF THE INVENTION

There is a critical need for effective strategies to treat neoplasms of the nervous system, particularly high grade gliomas, such as glioblastoma (GBM). Tumor and cancer cells have known vulnerability to changes in the electrochemical environment, but direct stimulation techniques have not been developed for tumors of the nervous system. In one embodiment, the present invention provides strong evidence to support a new treatment called intratumoral modulation therapy (IMT), which uses implanted electrodes and offers distinct advantages over existing therapies, including direct lesion targeting for continuous, focused treatment, adjustable stimulation settings to maximize benefit and lessen side-effects and low maintenance, concealed hardware for improved self-perception and quality of life. IMT may provide direct anti-cancer benefits, enable development of personalized gene therapies and enhance the effect of existing treatments to improve outcomes for patients with GBM and other systemic and nervous system tumors. The IMT of the present invention is for a chronic, i.e. permanent, implant to provide chronically active therapy in patients in need. The IMT paradigm of the present invention is designed for sustained therapeutic delivery of greater than 10,000 voltage pulses or cycles, including greater than 400,000 voltage pulses or cycles per hour, or even greater than 700,000 voltage pulses or cycles per hour.

In a first embodiment, the present invention provides for an intratumoral modulation therapy (IMT) method for chronically treating nervous system and systemic tumors in a patient including: (a) chronically implanting an electrode(s) adjacent to or within a site of the patient suspected of having tumor cells, such as adjacent to or within the tumor of the patient or adjacent or within a residual tumor bed, the electrode(s) having electrical leads connected thereto; and (b) generating continuous, alternating or pulsed electric stimulation and applying the electric stimulation through the electrical leads to the electrode(s) adjacent to or within the site, the continuous or pulsed electric stimulation being applied at a frequency or anatomical location that avoids neural entrainment or significant adverse neurological effects or significant adverse effects.

In one embodiment of the IMT method of the first embodiment, the continuous, alternating or pulsed electric stimulation is applied at about 0.1 milli-amps (mA) to about 4 amps (A).

In another embodiment of the IMT method of the first embodiment, the continuous, alternating or pulsed electric stimulation is applied at about 2 mA.

In another embodiment of the IMT method of the first embodiment, the method involves the application of voltages of about +/−1-10 V at a frequency of 500 Hz to 500 kHz or 1-10 V at a frequency of 500 Hz to 500 kHz. If the electric stimulation is applied at a location that avoids neural entrainment or significant adverse neurological effects, then the method involves the application of voltages of about +/−1-10 V at a frequency of 50 Hz to 500 kHz or 1-10 V at a frequency of 50 Hz to 500 kHz.

In another embodiment of the IMT method of the first embodiment, the method involves the application of voltages of about +/−1-10 V at a frequency of 500 Hz to 500 kHz or 1-10 V at a frequency of over 10 kHz to 500 kHz.

In another embodiment of the IMT method of the first embodiment, the method involves the application of 1-10 V at 500 Hz or more.

In another embodiment of the IMT method of the first embodiment, the method involves the application of voltages of about +/−1-2 V at a frequency of 200 kHz.

In another embodiment of the IMT method of the first embodiment, the method involves the application of voltages of about 4 V at a frequency of 130 Hz square wave.

In another embodiment of the IMT method of the first embodiment, the continuous or pulsed electric stimulation is applied at a frequency of more than 10 kHz.

In another embodiment of the IMT method of the first embodiment, the electric stimulation is pulsed electric current and the method involves the application of voltages pulses with a pulse width of less than 100 µs.

In another embodiment of the IMT method of the first embodiment, the electric stimulation is pulsed electric current and the method involves the application of more than 10,000 voltage pulses.

In another embodiment of the IMT method of the first embodiment, step (a) comprises chronically implanting a single electrode in the tumor or the site and implanting an extratumoral electrode.

In another embodiment of the IMT method of the first embodiment, the extratumoral electrode is implanted in a subgaleal or subdural spaces of the patient.

In another embodiment of the IMT method of the first embodiment, step (a) comprises chronically implanting multiple electrodes (i.e. more than one electrodes) within the tumor or the site or around the tumor or the site.

In another embodiment of the IMT method of the first embodiment, the method further comprises delivering genetic material to the tumor. In one aspect, the genetic material is associated with the expression of one or more genes. In another aspect, the genetic material is associated with the inhibition one or more of the following: gene expression and/or function, cell proliferation, cell migration, anti-apoptotic mechanisms, radiation resistance and drug resistance. In another aspect, the genetic material is siRNA or miRNA.

In one embodiment according to any of the previous IMT method embodiments, the method further comprises treating the patient with a therapeutic agent such as a chemotherapeutic and/or radiation. In one aspect of this embodiment, the therapeutic agent is temozolomide.

In another embodiment of the IMT method according to any of the previous embodiments, the tumor is a glial or non-glial tumor of the nervous or somatic system tissues.

The present invention, in a second embodiment, provides for a method of transferring or facilitating the transfer of genetic material to a tumor or cancer cell, the method including: (a) positioning at least one electrode adjacent to the tumor or cancer cell, the at least one electrode having electrical leads connected thereto; (b) generating an electric stimulus and applying the electric stimulus through the electrical leads to the electrode adjacent the tumor or cancer cell; and (c) delivering the genetic material to the tumor or cancer cell treated with the electric stimulus, thereby facilitating the transfer of the delivered genetic material to the tumor or cancer cell. In one aspect of this embodiment, the electrode may be chronically positioned adjacent to the tumor cell or cancer cell. In one aspect of this method, the method is in vitro or in vivo. In one aspect of this embodiment, the electric stimulus being applied at a frequency or anatomical location that avoids neural entrainment or significant adverse neurological effects.

The present invention, in a third embodiment, provides for a method for the treatment of a tumor or cancer in a patient including: (a) implanting at least one electrode adjacent to or within tumor or a site of the patient suspected of having tumor or cancer cells, the at least one electrode having electrical leads connected thereto; (b) generating an electric stimulus and applying the electric stimulus through the electrical leads to the electrode adjacent to the tumor or the site; and (c) during the electric stimulation, delivering to the tumor or the site genetic material associated with the inhibition of one or more of the following: gene expression, gene function, cell proliferation, cell migration, anti-apoptotic mechanisms radiation resistance and drug resistance, wherein a synergistic effect on the tumor treatment of the combination of the electric stimulation and the genetic material is substantially greater than the effect of each the electric stimulation and the genetic material taken alone. In one aspect of this embodiment, the electric stimulus being applied at a frequency or anatomical location that avoids neural entrainment or significant adverse neurological effects.

In one embodiment of the second and third embodiments, the electric stimulation is continuous alternating current, continuous alternating field, pulsed current or pulsed field.

In another embodiment of the second and third embodiments, the electric stimulus is applied at about 0.1 milliamps (mA) to about 4 amps (A).

In another embodiment of the second and third embodiments, the electric stimulus is applied at about 2 mA.

In another embodiment of the second and third embodiments, the method involves the application of voltage of about 1-10 V at a frequency of 50 Hz to 500 kHz or the application of voltage of about +/−1-10 V at a frequency of 50 Hz to 500 kHz.

In another embodiment of the IMT method of the second and third embodiments, the method involves the application of voltages of about +/−1-10 V at a frequency of 50 Hz to 500 kHz or 1-10 V at a frequency of over 10 kHz to 500 kHz In another embodiment of the IMT method of the second and third embodiments, the method involves the application of 1-10 V at 50-200 Hz.

In another embodiment of the second and third embodiments, the method involves the application of voltage of about +/−1-2 V at a frequency of 200 kHz.

In another embodiment of the second and third embodiments, the method involves the application of voltage of about 4 V at a frequency of 130 Hz.

In another embodiment of the second and third embodiments, the electric stimulation is applied at a frequency of more than 10 kHz.

In another embodiment of the second and third embodiments, the stimulus is pulsed electromagnetic stimulation and the method involves the application of voltages pulses with a pulse width of less than 100 µs.

In another embodiment of the second and third embodiments, the stimulation is pulsed stimulation and the method involves the application of more than 10,000 voltage pulses or cycles.

In another embodiment of the second embodiment, step (a) comprises implanting a single electrode in a tumor, around a tumor or tumor bed or anticipated tumor involved area having the tumor cell and implanting an extratumoral electrode.

In another embodiment of the second embodiment, step (a) comprises implanting multiple electrodes implanting multiple electrodes in a tumor or around a tumor, tumor bed or anticipated tumor-involved area.

In another embodiment of the second and third embodiments, the genetic material is associated with the expression of one or more genes. In one aspect, the genetic material is associated with the inhibition one or more of the following: gene expression and/or function, cell proliferation, cell migration, anti-apoptotic mechanisms, radiation resistance and drug resistance.

In another embodiment of the second and third embodiments, the genetic material is siRNA or miRNA.

In another embodiment of the second and third embodiments, the method further comprises treating the patient with a therapeutic agent (including chemotherapeutics) and/or radiation. In one aspect of this embodiment, the therapeutic agent is temozolomide.

In another embodiment of the second and third embodiments, the tumor or cancer cell is a glial or non-glial tumor cell of the nervous or a somatic tumor or cancer cell.

In another embodiment of the second and third embodiments, prior to step (a) the method comprises providing a device, the device including the at least one electrode to deliver the electric stimulus and one or more reference electrodes that are implanted in proximity to the at least one electrode that delivers the electric stimulus. In one aspect of this embodiment, the device further includes a cannula through which the genetic material or therapeutic agent is delivered, In another embodiment of the present invention, the site suspected of having tumor or cancer cells includes a residual tumor bed.

In another embodiment of the present invention the tumor or tumor cell is a glial or non-glial tumor cell affecting the nervous or a somatic tumor cell.

In another embodiment the present invention is a method for the treatment of a tumor or cancer in a patient including: (a) implanting at least one electrode adjacent to or within a tumor or a site of the patient suspected of having tumor or cancer cells, the at least one electrode having electrical leads connected thereto; (b) generating continuous alternating or pulsed electric stimulation and applying the electric stimulation through the electrical leads to the at least one electrode adjacent to or within the tumor or the site; and (c) during electric stimulation, treating the patient with a therapeutic agent, radiation, or both the therapeutic agent and radiation, wherein a synergistic effect on the tumor treatment of the combination of the electric stimulation and the therapeutic agent, radiation or both the therapeutic agent and radiation is substantially greater than the effect of each the electric stimulation, therapeutic agent, radiation, or both the therapeutic agent and radiation taken alone.

In another embodiment, the present invention is an implantable device comprising: (a) a hollow tube housing a cannula to deliver a biological material, (b) an electrode(s) to deliver an electric stimulus and (c) a reference electrode(s).

In another embodiment, the present invention is an implantable device comprising: (a) an electrode(s) to deliver an electric stimulus and (b) a reference electrode(s).

In another embodiment, the present invention is an implantable device comprising: (a) a hollow tube housing a cannula to deliver a biological material, (b) an electrode(s) to deliver an electric stimulus, (c) a reference electrode(s), (d) stimulus generator and (e) necessary connective wiring and hardware.

In another embodiment, the present invention is an implantable device comprising: (a) an electrode(s) to deliver an electric stimulus, (b) a reference electrode(s), (c) stimulus generator and (d) necessary connective wiring and hardware.

In another embodiments, the present invention relates to a synergistic use of electric stimulus in combination with a genetic material, a therapeutic agent, or the genetic material and therapeutic agent, in the treatment of a tumor. In aspect of the invention, the synergistic use includes the parameters described in the first, second and third embodiments, including: (a) wherein the electric stimulus is continuous alternating current or pulsed current, (b) wherein the electric stimulus is applied at about 0.1 milli-amps (mA) to about 4 amps (A), (c) wherein the electric stimulus is applied at about 2 mA, (d) wherein the method involves the application of voltage of about 1-10 V at a frequency of 50 Hz to 500 kHz or the application of voltage of about +/−1-10 V at a frequency of 50 Hz to 500 kHz, or 1-10 V at 50-200 Hz, (e) wherein the method involves the application of voltage of about +/−1-2 V at a frequency of 200 kHz, (f) wherein the method involves the application of voltage of about 4 V at a frequency of 130 Hz, (g) wherein the electric stimulation is applied at a frequency of more than 10 kHz, (h) wherein the electric stimulus is pulsed electric current and the method involves the application of voltages pulses with a pulse width of less than 100 µs, (i) wherein the electric stimulus is pulsed electric current and the method involves the application of more than 10,000 voltage pulses, (j) wherein the genetic material is associated with the inhibition of one or more of the following: gene expression, gene function, cell proliferation, cell migration, anti-apoptotic mechanisms, radiation resistance and drug resistance, (k) wherein the genetic material is siRNA or miRNA, (l) wherein the use further comprises using a therapeutic agent, (m) wherein the therapeutic agent is temozolomide, (n) wherein the tumor or tumor cell is a glial or non-glial tumor cell affecting the nervous or a somatic tumor cell.

In another embodiment of any of the previous embodiments, the electrode is insulated.

BRIEF DESCRIPTION OF THE DRAWINGS

The following figures illustrate various aspects and preferred and alternative embodiments of the invention.

DESCRIPTION OF THE INVENTION

Definitions

Figure 1:
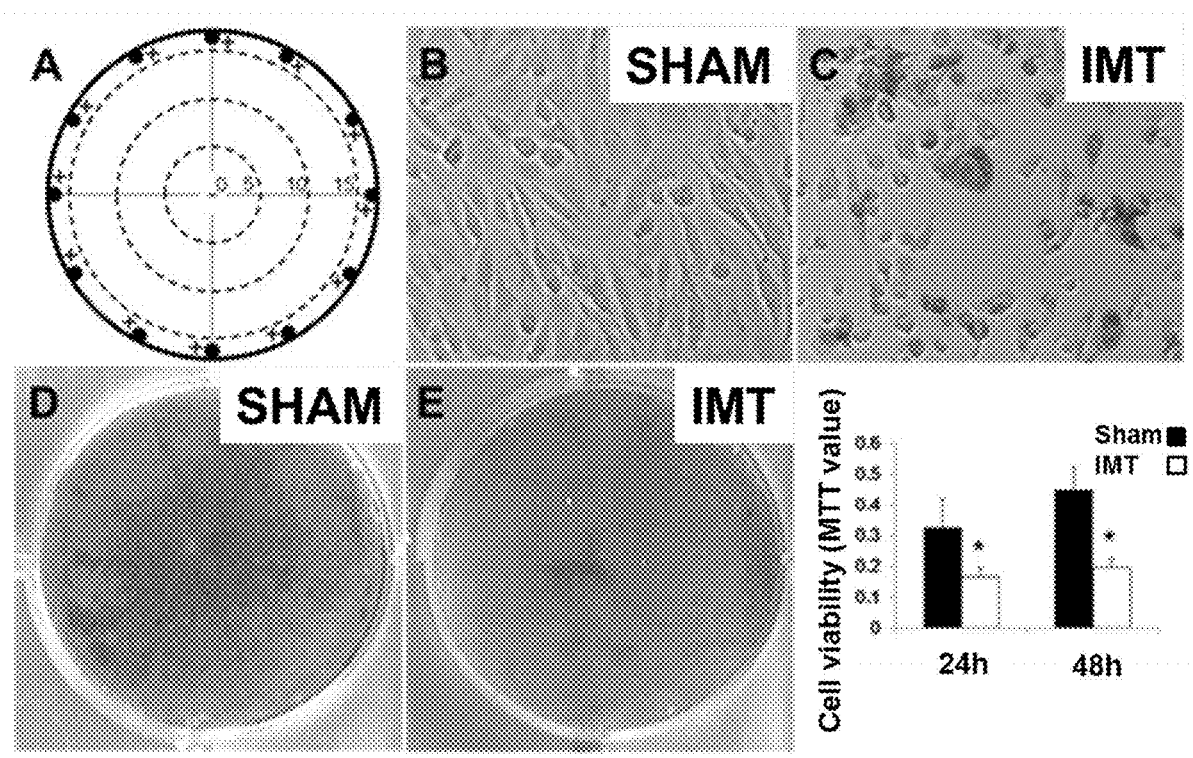
FIG. 1. In vitro IMT model. Panel A: Schematic representation of the in vitro IMT model. Panels B and C: brightfield microscopy (×20) photographs of primary patient GBM cells treated with 96 hours of sham conditions (panel B) or IMT (panel C) and stained with the membrane-impermeant dye, trypan blue. Cell viability was also evaluated using the spectral MTT (3-(4,5-dimethylthiazol-2-yl)-2,5-diphenyltetrazolium bromide (blue) stain) assay shown in the cell culture photographs of panels D (sham treated cells) and E (IMT treated cells). Panel F: histogram showing the mean cell viability in 3 primary patient GBM cell preparations treated with sham conditions or IMT for 24 or 96 hours (mean+standard deviation). (Asterisks; $P<0.05$.)
Figure 2:
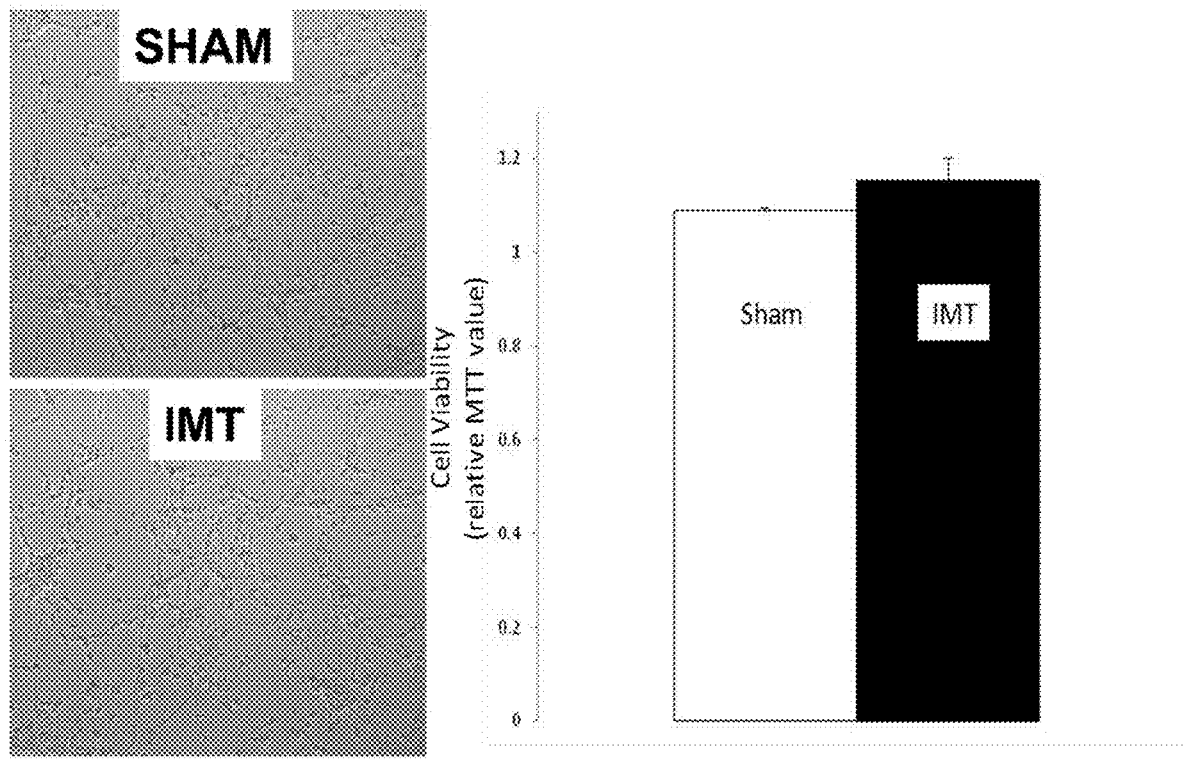
FIG. 2. Shown are photographs of embryonic rat neuronal cultures sham treated (panel A) or treated for 3 days with IMT (panel B) and imaged with bright field microscopy (×20) after exposure to trypan blue viability dye. Panel C is a histogram showing the relative viability in each group as measured with the MTT spectrophotometric assay.

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise. In order to aid in the understanding and preparation of the within invention, the following illustrative, non-limiting, examples are provided.

"Effective amount" refers to an amount of the composition that is capable of producing a medically desirable result in a treated subject. The methods of the present invention may be performed alone or in combination with other drugs or therapies.

"Subject" refers to a human or non-human mammal having or likely to develop a tumor.

By the term "treating" or "treatment", is meant reversing, minimizing, alleviating, substantially inhibiting the progress of a tumor, or preventing the formation or recurrence of a tumor.

Overview

An implantable device to deliver electrical stimulation, including alternating current, within tumor-affected brain regions may exploit the known electrosensitivity of GBM cells while providing targeted, sustained and titratable therapy for the subject patient. Electric stimulation delivered within the brain mandates pulse settings in line with clinical neuromodulation strategies (see below) rather than high voltage, cytoablative or electroporation currents. Chronic electric stimulation delivered within the brain mandates the avoidance of disrupting normal neurological function or producing disabling neurological symptoms (e.g., pain, motor contractions, sensory changes etc.). Adverse neurological effects may be avoided by focusing the treatment on tumor and tumor-affected regions of the nervous system that are inherently pathological (central nervous system or peripheral nervous system). In addition, the use of stimulation frequencies outside the range of neuronal entrainment (eg, >500 Hz) will also limit treatment-induced side effects.

The approach of the present invention is referred to as intratumoral modulation therapy or IMT when applied to the treatment of neoplastic disease. IMT is novel in the management of tumors, including tumors of the nervous and somatic system tissues. The present invention may also be used to prevent tumors from forming or recurring.

The IMT methods of the present invention may comprise the use of insulated or non-insulated stimulating or reference electrodes of various composition, number, size and configuration, to generate voltage-based, current-based or field-based IMT parameters.

Methods

The present invention, in one embodiment, provides for a method of treating a tumor in a subject. The method may include positioning an electrode adjacent to or within the tumor, and using the electrode to deliver an electrical stimulation to the tumor. The stimulation, in one embodiment, may be continuous current or pulsed current. The electrode may also be positioned adjacent to or within a residual tumor bed, i.e. a site from which a tumor was surgically removed so as to prevent the tumor from recurring.

IMT may entail surgical placement of electrodes adjacent to, in the vicinity of, or into target tumors or residual tumor beds, including tumors of the nervous system, or somatic system tissue tumors such as lung, breast, prostate, melanoma, liver, colon, pancreas and so forth, with control via a remote-accessed pulse generator, which may be housed in the subcutaneous tissues of the chest or it may be an external pulse generator (i.e. non-implanted). The pulse generator may generate continuous current (including alternative current or direct current) or pulsed current. The current may be characterized by amplitude (volts), current (amps), frequency (Hz), and pulse width (microseconds). Preferably, the pulse generator may generate frequencies that avoid neuronal entrainment.

A typical IMT lead may be an insulated lead comprising insulated or non-insulated electrodes, which may be composed of platinum/iridium and spaced millimetres apart along the length of the lead. One or multiple leads may be implanted in a target tumor or regions to provide in situ low dose of continuous stimulation; and/or implanted in the extra-cranial tissue planes. The lead is connected to a pulse generator (PG), which serves as a controller and power source. The PG typically includes a battery and circuitry for telemetered communication with an external programming device used to adjust, or "tune," the IMT lead stimulation parameters, which may include stimulation frequency, amplitude, pulse width (or wavelength), and contact configuration (that is, the selection of which electrodes are utilized from among the electrodes available on a lead, and, if two or more electrodes are active, the relative polarity of each). These parameters may be initially set during implantation surgery and may then further fined-tuned in the outpatient clinic or in a doctor's office following surgery to maximize therapeutic benefit and minimize undesirable stimulation-induced side effects.

In one embodiment, the IMT system for chronic treatment of a tumor may include a pulse generator, a treatment electrode, a reference electrode and electrical leads connecting the treatment and reference electrodes to the pulse generator. The pulse generator may be an implantable device that generates frequencies that avoid neuronal entrainment, i.e. frequencies of about 500 Hz or more. If the implantable device is placed in a location of the nervous system (peripheral and central) that would not be predispose to neuronal entrainment or pose adverse symptoms from the treatment, then frequencies lower than 500 Hz may be used, such as 50 Hz or above, including 130 Hz and 200 Hz.

In one embodiment of the present invention, the continuous or pulsed stimulation may be applied at about 0.1 milli-amps (mA) to about 4 amps (A), including any mA or A there in between, such as 0.2 mA, 0.3 mA, 0.4 mA, 0.5 mA, 0.6 mA, 0.7 mA, 0.8 mA, 0.9 mA, 1 mA, 1.5 mA, 2 mA, 2.5 mA, 3 mA, 3.5 mA, 4 mA, 4.5 mA, 5 mA and so forth, and 1 A, 1.5 A, 2 A, 2.5 A, 3 A, 3.5 A. As such, in another embodiment, the pulsed or continuous stimulation is applied at about 2 mA. If the PG generates direct current, then the PG may include an inverter or device that will convert direct current to alternating current.

Continuous alternating or pulsed current may be applied at about +/−1-10 V at a frequency of 50 Hz to 500 kHz or any combination thereof. For example, continuous alternating current may be +/−1-2 V at a frequency of 200 kHz sinusoidal wave or it may be +/−4 V at a frequency of 130 Hz. The frequency may also range over 10 kHz to 500 kHz.

In one embodiment of the present invention, the PG generates pulsed current, which may be applied at about 0.1 milli-amps (mA) to about 4 amps (A), including any mA or A there in between, such as 2 mA.

Preferably, the frequencies used in the methods of the present invention would not produce neuronal entrainment. 500 Hz or more may be used to avoid neuronal entrainment.

The pulsed current may be applied at about 1-10 V at a frequency of 50 Hz to 200 kHz or any combination thereof. For example, the pulsed current may be 1-2 V at a frequency of 200 kHz or it may be 4 V at a frequency of 130 Hz square wave.

The IMT method may involve the application of voltages pulses with a pulse width of less than 100 μs. The period (interval between pulses or pulse spacing) may be less than 1 second. In another embodiment, the period may be less than 500 msec. In another embodiment, the period may be less than 20 msec. In yet another embodiment, the period may be 5 μsec for the high freq, and less than 20 msec for low freq IMT. At the low frequency the period may be less than 10 msec or less than 8 msec or less than 7 msec. It should be understood that when the period is less than, let say, 10 msec, this period includes any range in between the integers, for example, 9.9, 9.8, 9.7, 9.6, 9.5, 9.4, 9.3, 9.2, 9.1, 9, 8.9, 8.8 and so forth msec.

The IMT method may involve the application of more than 10,000 voltage pulses. The IMT of the present invention may be for a permanent implant to provide chronically active therapy in patients in need.

IMT may induce caspase activation and apoptotic death of GBM cell lines, patient-derived GBM cells and in F98 rat GBM tumors. Post-mitotic neurons showed no significant loss of viability with IMT, consistent with a selective action on proliferative, neoplastic cells. IMT also produces a dramatic sensitization of GBM cells to TMZ chemotherapy (FIGS. 1-8). There have been no major discrepancies in the efficacy of treatment achieved in genetically unscreened specimens, suggesting the mechanism of IMT is independent of the tumor molecular profile.

Electro-Gene Therapy Using IMT

The present invention, in another embodiment, provides for a method of transferring genetic material to a tumor/cancer cell, the method may include: (a) positioning an electrode adjacent to the tumor/cancer cell, the electrode having electrical leads connected thereto; (b) generating an electric stimulus and applying the electric stimulus through the electrical leads to the electrode adjacent the cancer cell; and (c) delivering the genetic material to the tumor cell treated with the continuous alternating or pulsed electrical stimulation.

The electrical stimulation may be continuous current or pulsed current.

In one embodiment of the present invention, the current may be applied at about 0.1 milli-amps (mA) to about 4 amps (A), including any mA or A there in between. As such, in another embodiment, the current is applied at substantially 2 mA.

Continuous alternating stimulation may be applied at about +/−1-10 V at a frequency of 50 Hz to 200 kHz or any combination thereof. For example, continuous alternating current may be +/−1-2 V at a frequency of 200 kHz sinusoidal wave or it may be +/−4 V at a frequency of 130 Hz.

Direct or pulsed current may be applied at about 1-10 V at a frequency of 50 Hz to 200 kHz or any combination thereof. For example, the current may be 1-2 V at a frequency of 200 kHz or it may be 4 V at a frequency of 130 Hz square wave. Another example may be the application of 1-10 V at 50-200 Hz. Another example may be the application of frequency of over 10 kHz to 200 kHz.

The method may involve the application of voltages pulses with a pulse width of less than 100 μs. The method may involve the application of more than 10,000 voltage pulses.

Figure 9:
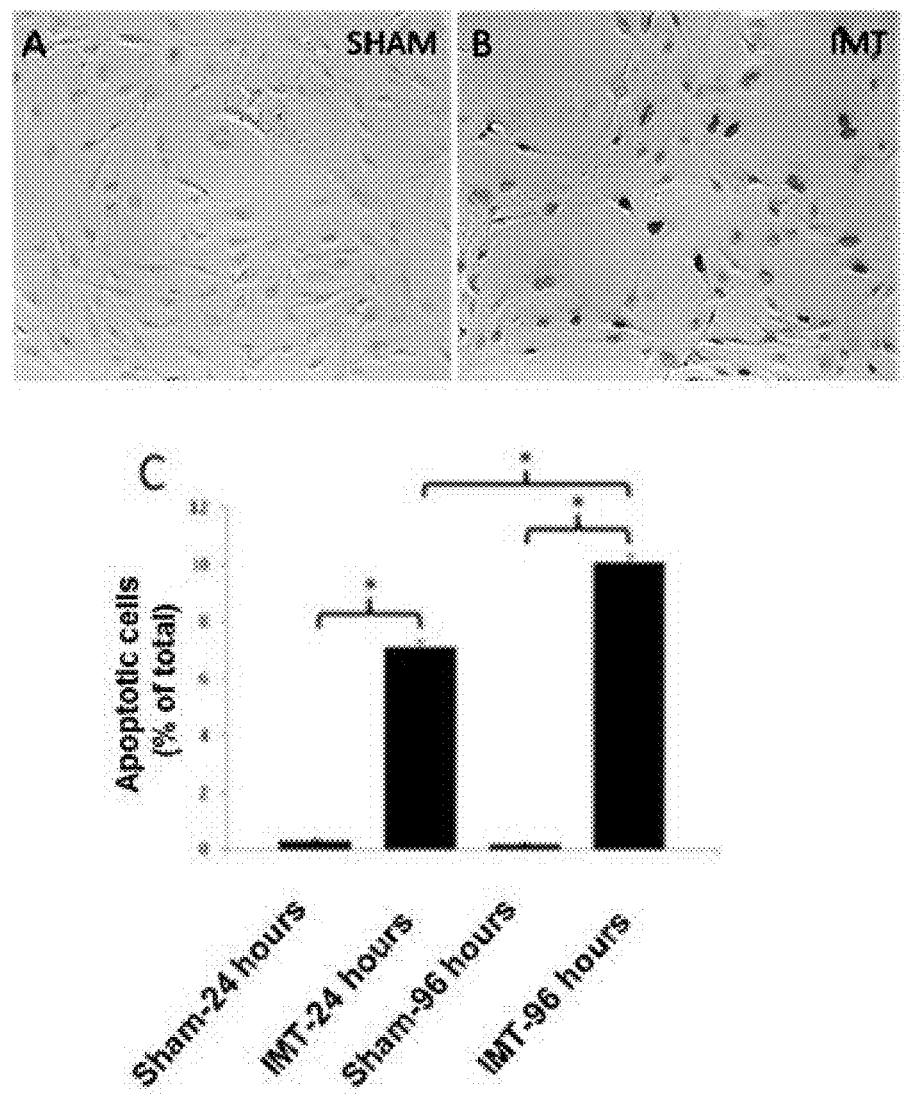
FIG. 9. A: photograph of GBM cultures under sham conditions; B: photograph of GBM cultures under IMT treatment; C: histogram illustrating quantified TUNEL cells. TUNEL-positive GBM cells were rarely seen with sham conditions (A), but abundant following IMT (B).
Figure 10:
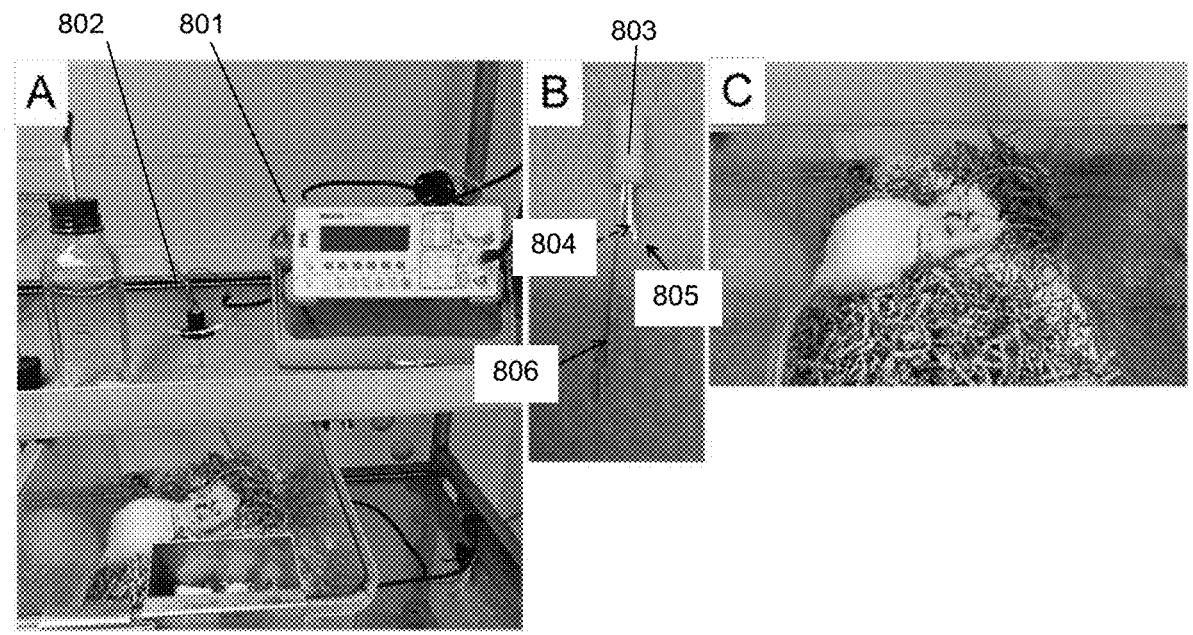
FIG. 10. A: Photograph of an animal receiving IMT in its home cage. The therapy is delivered using a waveform generator (top of picture) connected to an indwelling brain electrode via a commutator that allows free movement of the animal at all times B: Photograph of a cannula electrode construct. C: Closer view of the animal of panel A.
Figure 11:
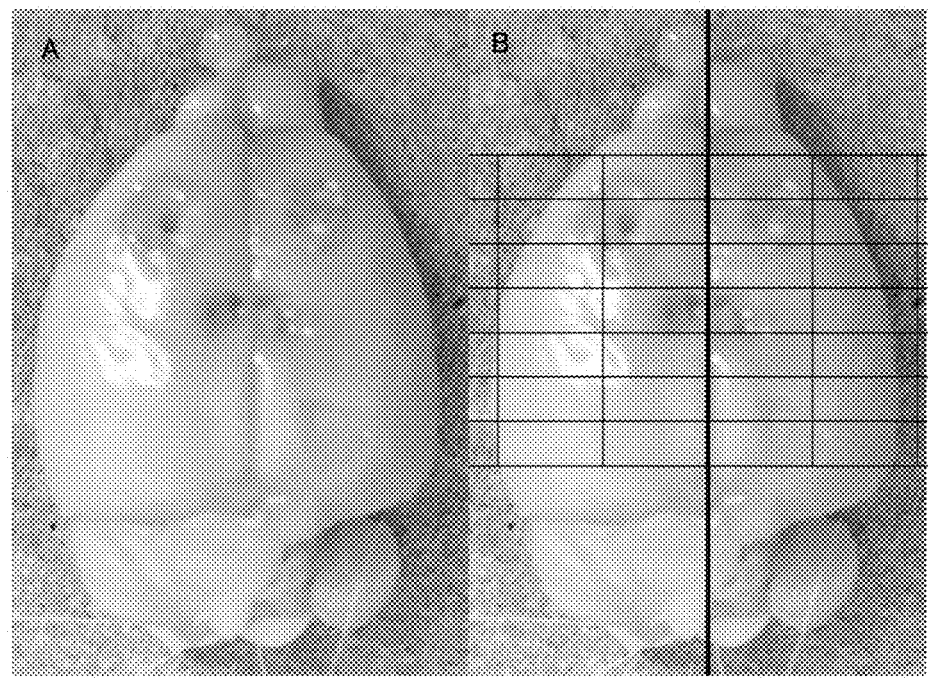
FIG. 11. A-B: Photographs of an extracted rat brain that housed bilateral GBM tumors in the striatum. IMT implants had been placed bilaterally (now removed) but only activated on the right side. Note the IMT-mediated reduction in hemispheric volume on the right compared to the left. The image of panel B shows the same brain of panel A with an overlaid grid for size calibration.

Specific inhibitors are unavailable for most newly identified molecular targets for GBM, however small interfering RNA (siRNA) are highly effective for reducing expression of specific genes and offer significant clinical promise. Unfortunately, poor cellular uptake remains a barrier to practical application, as these molecules do not readily cross cell membranes (12). Lipid-based carriers can be problematic, with variable efficacy and uptake by endosomes vulnerable to immune stimulation. Electric fields have been used for decades to enhance uptake of large or charged molecules into tumor cells. Long duration/low intensity pulses drive migration of charged molecules across cell membranes (i.e., electrophoresis) whereas short duration/high intensity stimuli produce hydrophilic pores through which charged substances may pass (i.e., electroporation) (13, 14). Neither electrophoresis nor electroporation have been described with IMT-type stimulation in GBM. The heat shock protein, HSP27, was chosen as a prototypic target for IMT-related studies due to its roles in cancer cell proliferation, migration, anti-apoptotic mechanisms and drug resistance (15-17). Other heat shock proteins are also involved in tumor-promoting activities, including therapeutic resistance mechanisms (22, 23). As with many of these proteins, there are no known selective natural or synthetic protein inhibitors and targeted interruption of their expression or function requires gene silencing strategies. siRNA-mediated HSP27 inhibition reduces viability and produces robust chemoradiation sensitivity in treatment-resistant GBM cell lines (18-20). The same robust effects are difficult to achieve in patient-derived specimens. With concurrent IMT, however, a dramatic increase in cytoplasmic siRNA in nearly every cell exposed was achieved (FIG. 9) and this was associated with a robust knockdown of HSP27 protein levels and potentiation of IMT-mediated GBM cell death (FIGS. 10, 11). These results indicate that IMT potently facilitates the uptake of therapeutic genetic material to produce a specific and robust response in patient GBM cells.

Table 1 provides exemplary (i.e. non-limiting) specific parameters and ranges of parameters that may be used to carry out the present invention, either for the IMT method or the method of transferring genetic material into a cell of the present invention.

TABLE 1

| | |
|---|---|
| Frequency | Range: 50 Hz-500 kHz |
| Voltage | Range: 1-10 V |
| Duty Cycle | Range: 0.45%-50% or higher |
| Pulse width | Range: 2.5 μsec-90 μsec or more |
| Period | Range: 5 μsec-20 msec |
| # pulses | Range >10,000 |

The specific examples below are to be construed as merely illustrative, and not limitative of the remainder of the disclosure in any way whatsoever. Without further elaboration, it is believed that one skilled in the art can, based on the description presented herein, utilize the present invention to the full extent. All publications cited are incorporated by reference. Any mechanism proposed below does not in any way restrict the scope of the claimed invention.

Example 1—In Vitro IMT Model

1. Materials and Methods
GBM Tissue Preparation and Cell Cultures

This study was approved by the Research Ethics Board at the University of Western Ontario (Approval #17290). GBM specimens were obtained at the time of operative resection and placed immediately into phosphate-buffered saline (PBS) with 0.5% fetal bovine serum (FBS; Life Technologies, Burlington, ON, Canada). The tissue was washed, digested and filtered through a 100-μm cell strainer. Samples were then centrifuged and resuspended in Dulbecco's modified Eagle's medium (DMEM; Wisent Bioproducts, St. Bruno, PQ, Canada) supplemented with 10% FBS, 1% non-essential amino acids and 1% penicillin/streptomycin (Life Technologies) before plating to a 35-mm dish for 30 min to allow blood cells to separate. The upper cell suspension was then transferred to two wells of a 24-well plate, freshly pre-coated with 10 μg/ml poly-L-lysine (Trevigen Inc., Gaithersburg, Md., USA) and incubated at 37° C. with 5% $CO_2$. Cultures were passaged at approximately 80% confluence and split 1:2 using 0.25% trypsin with 0.53 mM ethylenediaminetetraacetic acid (EDTA; Wisent). The medium was changed twice per week. All assays were conducted using GBM cells from cultures at passages 4 through 12.

Human LN229 GBM cells (ATCC, Manassas, Va., USA) were maintained in DMEM supplemented with 10% FBS, 1% nonessential amino acids and 1% penicillin/streptomycin (Life Technologies) at 37° C. in a humidified atmosphere of 5% $CO_2$. The cells were passaged every 2-3 days using 0.25% trypsin-EDTA (Wisent). At the exponential phase of growth, cells were seeded in 35 mm wells of a 6-well plate in maintenance medium for 24 h prior to treatments.

Embryonic Rat Neuronal Cultures

This protocol met the standards of the Canadian Council on Animal Care and was approved by the University of Western Ontario Animal Use Subcommittee (Approval #2014-016). IMT was performed in primary neuronal cultures (N=3) to determine its effects on post-mitotic neural cells. As primary human neurons are not readily available, these studies were conducted in preparations isolated from embryonic rat brain. Pregnant female Wistar rats (Charles River, Montreal, PQ, Canada) were sacrificed by cervical dislocation for surgical removal of E18 embryos. Cortices from each embryo were extracted and placed in a 14 ml conical tube containing 1.8 ml of Hank's balanced salt solution (HBSS; Wisent) and centrifuged at 4000×g for 1 min at room temperature. HBSS was aspirated and 1.8 ml of solution A containing 5 ml HBSS, 6 μl $MgSO_4$ (1 M) and 2 ml trypsin (Sigma Aldrich, St. Louis, Mo., USA) were added. The tube was mixed well, ensuring the neurons were free floating, and placed in an automated rotator at 37° C. for 25 minutes. After rotation, 3.6 ml of solution B containing 7 ml HBSS, 8 μl $MgSO_4$ (1 M), 175 μl DNase1 (10 mg/ml) and 112 μl trypsin inhibitor (100 μg/ml, Roche Life Sciences, Indianapolis, Ind., USA) was added to the conical tube and mixed for 2 minutes, centrifuged at 4000×g for 5 min at room temperature, after which the HBSS was aspirated. Finally, 6 ml of a solution C containing 20 ml of HBSS, 48 μl $MgSO_4$ (1 M), 1.3 ml DNase1 (10 mg/ml), and 1 ml trypsin inhibitor (100 μg/ml) was added to the resulting cell pellet (Roche). These cells were transferred to a 50 ml falcon tube and another 6 ml of solution C was added. The cells were titrated, centrifuged at 4000×g for 5 minutes and the supernatant aspirated. The cell pellet was resuspended in 36 ml of neurobasal plating media containing 96% neural basal media (Wisent), 2% B27 supplement, 0.8% $N_2$ Supplement, 0.5% penicillin/streptomycin, 0.25% Glutamax (Life Technologies), and 0.1% Amphotericin B solution (Sigma Aldrich). Cells were counted with a hemocytometer, plated in 35 mm wells coated with 7% poly-L-Ornithine (Sigma Aldrich) at density of $0.5 \times 10^6$ cells/well and kept in an incubator at 37° C. with 5% $CO_2$. The medium was changed on the third day of culture, then wells were fitted with the IMT apparatus (see below) for delivery of 72 h of sham or IMT conditions.

In Vitro IMT Model

The in vitro IMT model was developed by the applicant's laboratory and consists of calibrated 35 mm wells fitted with a central stimulating electrode and peripheral strip electrode to deliver chronic stimulation using parameters typically with low voltage (<10V) and a broad range of frequencies and waveforms. The parameters used in this study are 4 V of 130 Hz and 2 V of 200 kHz. In one model, IMT is delivered using a 1.3 mm cathodic electrode placed in the centre of the cell field, with an anodic electrode at the periphery (FIG. 1A). Electrodes are composed of clinical grade platinum or platinum/iridium alloy, with square or sinusoidal waves produced by a waveform generator and delivered continuously. Various durations of IMT treatment have being tested and found that 72 hours is practical and efficacious for cultured GBM cells and will be applied to the in vitro component of this study. IMT experiments are run in parallel with a battery of control conditions. This work demonstrated robust tumoricidal effects of IMT with either low or high frequency parameters, and marked potentiation of therapeutic effect when combined with TMZ treatment (FIGS. 1-7).

GBM cells ($2 \times 10^5$ cells in 2 ml maintenance DMEM) were transferred to the 35 mm wells in standard 6-well plates and allowed to grow to ~70% confluence before treatment. A clinical grade, platinum-based reference strip electrode (AD-Tech, Racine, Wis., USA) around the periphery and a stimulating electrode (Medtronic Ltd., Brampton, ON, Canada) in the centre of the well. The electrodes were connected to a waveform generator set to produce monophasic, square-wave pulses of 4 volts, with pulse width of 90 μsec and frequency of 130 Hz. This setting is in the range of that commonly used in clinical neuromodulation treatment for symptoms of movement disorders, such as Parkinson's disease (11). Control wells (i.e. sham-treated) were fitted with electrodes but no current was delivered. Treatment durations between 24-96 h were used to allow adequate time for antitumor effect while avoiding the need for medium change once IMT was initiated. Thus, all intact GBM cells, adherent and floating, contributed to the viability measures described below. GBM cells treated with chemotherapy were plated with DMEM containing temozolomide (50 µM; Sigma Aldrich) in 35 mm wells fitted with the IMT apparatus and received 72 h of concomitant IMT or sham conditions. The 50 µM temozolomide concentration reflects clinically relevant levels corresponding to the in vivo plasma concentration of 150 mg/m2 in the adjuvant phase of GBM treatment (24).

Concomitant IMT and HSP27 Knockdown

Primary human patient GBM cells ($1 \times 10^5$ cells in 2 ml maintenance DMEM) were seeded into one 35 mm well equipped with the IMT system and allowed to grow to ~70% confluence. Cells were transfected with siRNA targeting human HSP27 mRNA (50 nM) or an equivalent concentration of non-specific control siRNA (siRNA Universal Negative Control, Sigma Aldrich) using jetPRIME™ transfection reagent (Polyplus Transfection, New York, N.Y., USA) (18). The culture medium was replaced with 210 µl of jetPRIME-siRNA complex in 2 ml DMEM with 10% FBS. The transfected cells were incubated for 48 h at 37° C. with 5% $CO_2$. In the IMT-siRNA conditions, IMT was initiated at the time of transfection and maintained for the entire 48 h, after which the extent of target knockdown and GBM cell viability were assessed.

Cell Viability Assays

Cell viability was evaluated using the 3-(4,5-dimethylthiazol-2-yl)-2,5-diphenyltetrazolium (MTT) spectral analysis (Sigma Aldrich). This colorimetric assay measures the reduction of yellow MTT by mitochondrial succinate dehydrogenase to an insoluble, dark purple Formosan product. Immediately following the GBM cell treatments described above, MTT (80 µl at 5 mg/ml) was added to the 35 mm wells and incubated for 3 hours at 37° C. in a humidified 5% $CO_2$ atmosphere. The cells were then lysed to release the purple Formosan product by the addition of 600 µl dimethyl sulfoxide for 15 min at room temperature. Absorbance was measured using an enzyme-linked immunosorbent assay plate reader (Fisher Scientific, Nepean, ON, Canada). Cell viability was estimated using optical density values at 570 nm with references at 655 nm detected in each well.

Trypan blue exclusion was used as a confirmatory, qualitative measure of cell viability. Briefly, 0.1 ml of a 0.4% trypan blue solution (Lonza, Walkersville, Md., USA) was added for every 1 ml culture media and the cells then incubated for 2 min at room temperature. Brightfield images of cells were obtained using a Motic AE31 inverted microscope fitted with an Infinity1-3 scientific complementary metal-oxide semiconductor camera (Lumenera Corp., Ottawa, ON, Canada).

Flow Cytometry

An Annexin V Apoptosis Detection Kit with propidium iodide (PI; BioLegend, San Diego, Calif., USA) was used for identification of apoptotic and dead cells, as per the manufacturer's instructions. Cell fractions were analyzed using a Becton Dickinson LSR II SORP flow cytometer running FACSDiva software (BD Biosciences, Mississauga, ON, Canada). Cells were first gated on forward scatter (FSC-) versus side scatter (SSC-) characteristics before excluding doublets using consecutive gating FSC-Area versus FSC-Width and SSC-Area versus SSC-Width plots. The populations of annexin V+/PI−, annexin V+/PI+, annexin V−/PI+ and annexin V−/PI− were then calculated with quadrant gates. Approximately 30,000 single cells were acquired per sample at a maximum event rate of 5,000 events per second. Data were analyzed using FlowJo v 9.6.3 (TreeStar, Inc., Ashland, Oreg., USA).

Western Blot Analysis

Cells were collected in lysis buffer (50 mM Tris HCl, 150 mM NaCl, 1% Nonidet P40, pH 7.4) supplemented with SIGMAFAST™ Protease Inhibitor cocktail (1:10), incubated on ice for 15 min then sonicated (Sigma Aldrich). The cell lysates were centrifuged and the protein supernatant collected. Twenty micrograms of each protein extract were separated on a 10% sodium dodecyl sulphate polyacrylamide gel and transferred electrophoretically to Immun-Blot® membranes (Bio-Rad Laboratories Ltd., Mississauga, ON, Canada). The membranes were blocked, then incubated overnight at 4° C. with primary antibodies to HSP27 (1:1000), HSP90 (1:800), or activated caspase-3 (1:500; EMD Millipore Corp., Billerica, Mass., USA). Membranes were washed then incubated with a horseradish peroxidase-conjugated secondary antibody (1:3,000; Bio-Rad) for 1 hour at room temperature. Peroxidase activity was visualized using an enhanced chemiluminescence and detection system imager (GE Healthcare Biosciences, Piscataway, N.J., USA). Membranes were then stripped, blocked and re-probed with an anti-β-actin antibody (1:5,000; Abcam Inc, Toronto, ON, Canada) to assess protein loading.

Immunofluorescence Labeling of Activated Cspase-3 and Confocal Microscopy

GBM cells were plated on 12 mm round cover slips (VWR International, Mississauga, ON, Canada) and collected 24 h after treatment. Cells were washed, fixed in 4% paraformaldehyde and permeabilized prior to blocking with 1% bovine serum albumin (EMD Millipore Corp.) and incubation with a primary rabbit antibody to activated caspase-3 (1:100, EMD Millipore Corp.) overnight at 4° C. Cells were then washed and incubated with Alexa Fluor® 546 goat anti-rabbit IgG secondary antibody (1:200; Life Technologies) for 1 h at room temperature and counterstained with 4'-6-diamidino-2-phenylindole (DAPI; Life Technologies) for nuclear visualization. Control cover slips were processed in parallel without primary antibody. Cells were imaged using a Zeiss LSM-510 META laser-scanning microscope with a Zeiss 63× NA 1.4 oil immersion lens, appropriate filters and AIM software (Carl Zeiss GmbH, Jena, Germany, EU).

Statistical Analysis

Paired and multiple comparisons were made with Student's t-test or one-way analysis of variance (ANOVA) followed by Newman-Keuls post-hoc analysis, respectively (SigmaStat, Systat Software Inc., San Jose, Calif., USA). All data are presented as the mean±standard deviation and comparisons were considered significant at $p<0.05$.

2. Results

IMT Induces GBM Cell Death

LN229 GBM cells and GBM cells derived from three patient primary tumors were treated with 96 hours of sham conditions (FIG. 1B) or IMT (FIG. 1C) and stained with the membrane-impermeable dye, tyrpan blue. Note the reduced cell density, extensive pyknosis and trypan blue uptake in the IMT-treated preparations (FIG. 1C) compared to the sham condition (FIG. 1B). Cell viability was also evaluated using the spectral MTT assay in sham (FIG. 1D) and IMT-treated (FIG. 1E) cells. The sham cultures (FIG. 1D) stained purple with MTT and extended across most of the culture well. In contrast, the IMT-treated preparations (FIG. 1E) exhibited markedly diminished, patchy staining, consistent with extensive GBM cell death. The histogram of FIG. 1F shows the mean cell viability in 3 primary patient GBM cell preparations treated with sham conditions or IMT for 24 or 96 hours (mean+standard deviation). Note the significant loss of viability with IMT at both time points (asterisks; P<0.05).

In contrast to the impact on GBM cells, IMT did not produce overt alterations in morphology or viability of rat post-mitotic neurons. Embryonic rat neuronal cultures were treated for 3 days with sham conditions (FIG. 2A) or IMT (FIG. 2B) and imaged with brightfield microscopy (×20) after exposure to trypan blue viability dye. No significant labeling or morphological changes were identified after IMT in these cells. The histogram of FIG. 2C shows the relative viability in each group as measured with the spectral MTT assay (mean+standard deviation). No loss of neuronal viability was found with IMT (relative MTT values: sham=0.63±0.00; IMT=0.64±0.02, p=0.36, FIG. 2C).

Apoptosis and Enhanced Chemotherapeutic Effect in GBM Cells Treated with IMT

The mechanism of IMT-mediated GBM cell death was evaluated by immunolabeling of activated caspase-3, a marker of apoptosis, and flow cytometric detection of the apoptosis and cell death markers, annexin and PI, respectively.

Figure 3:
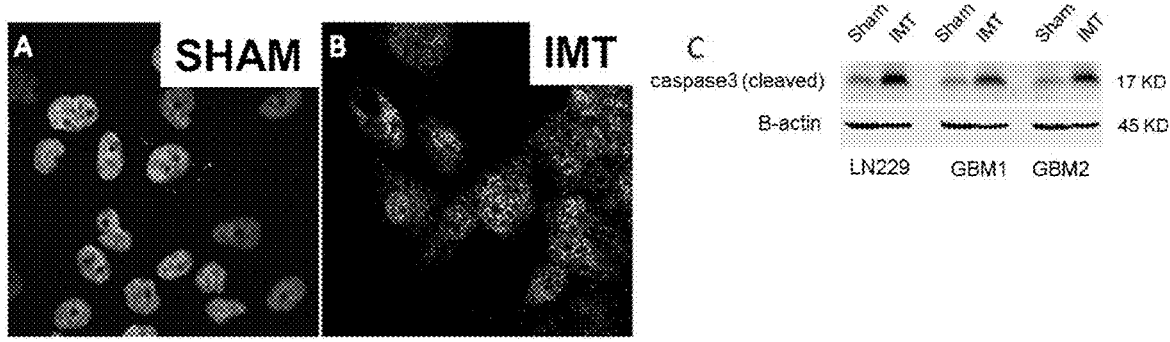
FIG. 3. IMT-mediated apoptosis correlates with caspase-3 activation (cleaved caspase-3) in GBM cells. Panels A and B: Confocal imaging (×63 magnification) of sham (A) and IMT-treated (B) primary patient GBM cells immunolabeled for activated caspase-3 (stains red) and counterstained with the nuclear dye, DAPI (stains blue). Panel C is a representative western blots are shown that confirm the immunocytochemistry data.

IMT reliably and robustly increased the cellular level of activated caspase-3 in immortalized and primary patient GBM cells, consistent with the pyknotic morphology of IMT-treated GBM cells and indicative of an apoptotic death (FIG. 3).

Figure 4:
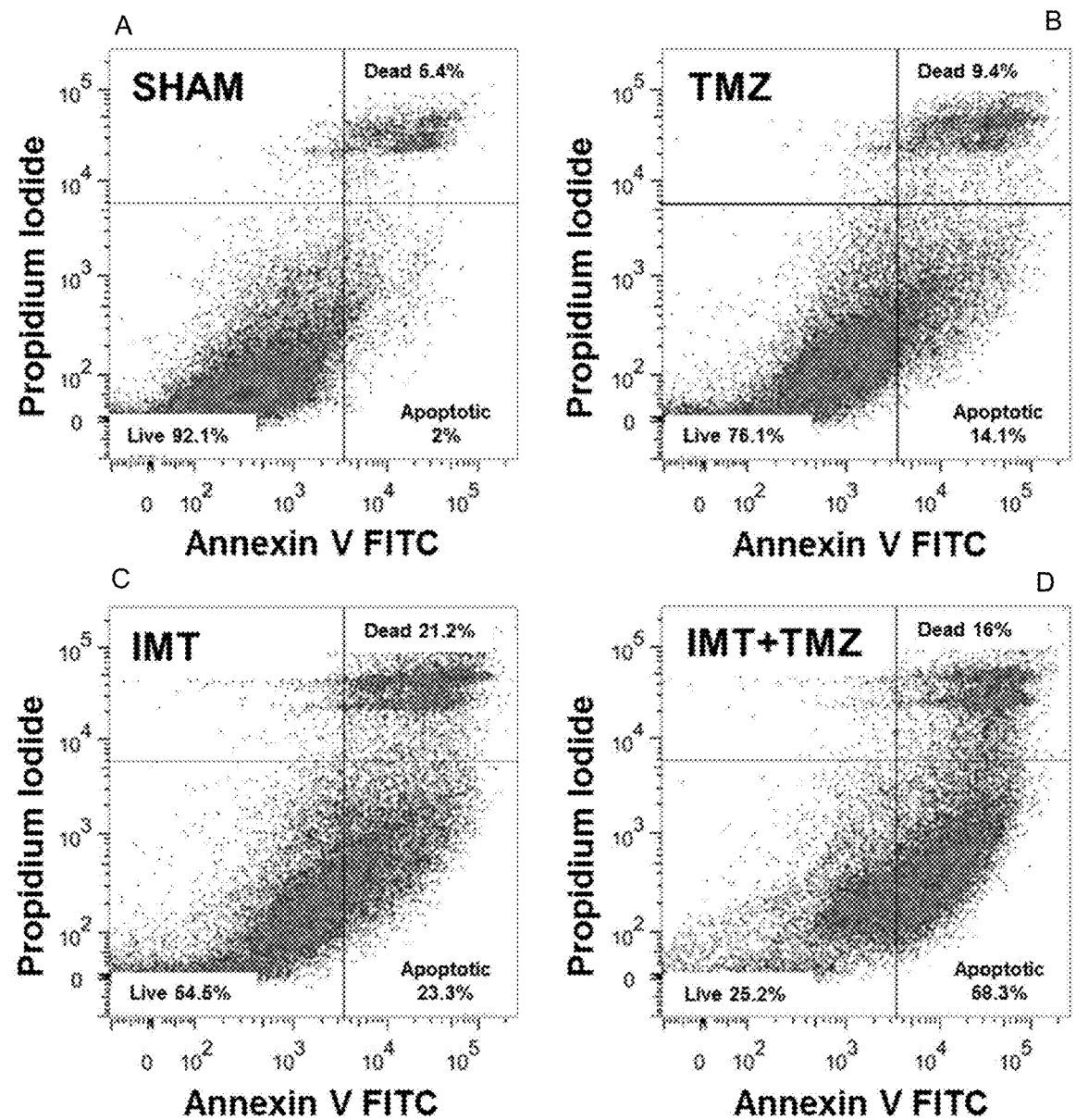
FIG. 4. A-D: Representative flow cytometry scatterplots showing annexin and propidium iodide (PI) labeling of apoptotic and dead patient GBM cells, respectively, after 72 hours of the indicated treatment. There were approximately 30,000 cells analyzed for each treatment condition. Note the markedly elevated fractions of apoptotic (annexin-positive) and dead (annexin and PI-positive) cells with the combination of IMT and TMZ, relative to those observed with sham or either stand-alone treatments. These studies were performed in triplicate using primary GBM cells from 3 different patients. Potent anti-tumor effects of combined IMT and TMZ in GBM Flow cytometry with PI and annexin labeling showed a marked increase in dead or apoptotic GBM cells (cells in right upper and lower quadrants, respectively) with combination IMT+TMZ therapy (lower right panel D), compared to sham conditions (upper left panel, A), or treatment with either IMT (lower left panel, C) or TMZ (upper right panel, B) alone.
Figure 5:
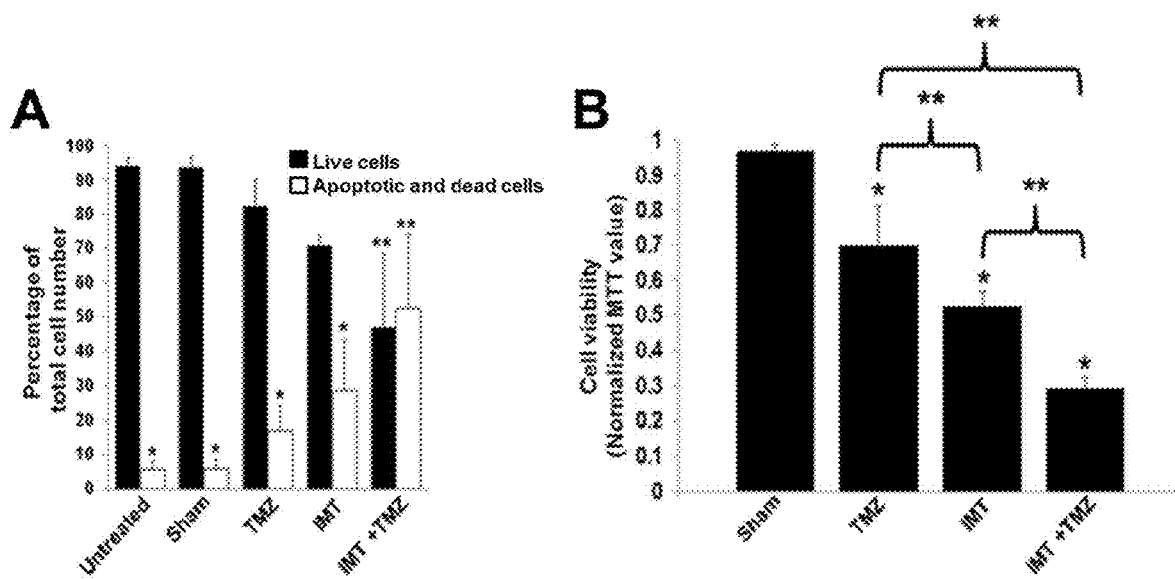
FIG. 5. Panel A: Histogram of the flow cytometry data showing the percentage of live and apoptotic/dead GBM cells following the indicated treatments. Single asterisk indicate significant difference between the percentage of live and apoptotic/dead cells within all groups ($P<0.05$, ANOVA). Double asterisks indicate a significant difference between the live or apoptotic/dead fractions and the respective value obtained from untreated cells ($P<0.05$, ANOVA). Panel B: Histogram of the MTT (temozolomide) assay measured GBM cell viability following control, single agent TMZ or IMT, and concomitant IMT and TMZ treatments. Relative values were normalized to those of untreated cells. Single asterisks indicate significant difference from sham treatment values. Double asterisks indicate a significant difference between the indicated treatment pairs ($P<0.05$, ANOVA). For both flow cytometry and MTT studies, the duration of treatment was 72 hours and each measure shown represents the mean+standard deviation for primary GBM cells from 3 patients.

Flow cytometry was performed in triplicate on primary GBM cells from three patient specimens (~30,000 cells per treatment condition for each patient specimen) to detect the apoptotic marker, annexin, and uptake of the membrane impermeant dye, PI (FIGS. 4 and 5A). Note in FIG. 4 the markedly elevated fractions of apoptotic (annexin-positive) and dead (annexin and PI-positive) cells with the combination of IMT and TMZ, relative to those observed with sham or either stand-alone treatments. The flow cytometry scatterplots of FIG. 4 illustrate dead (upper right quadrant), apoptotic (lower right quadrant) and live (lower left quadrant). The flow cytometry scatterplots of FIG. 4 show that under sham IMT treatment (A) 5.4% of the cells are dead, 2% apoptotic and 92.1% are live; under TMZ (B) 9.4% of the cells are dead, 14.1% are apoptotic and 76.1% live; under IMT (C), 21.2% of the cells are dead, 23.3% apoptotic and 54.5% live; while under both TMZ+IMT treatment (D), 16% of the cells are dead, 58%. 3% apoptotic and 25.2% live. The combined fraction of apoptotic (annexin+) and dead (annexin+ and PI+) GBM cells rose dramatically from untreated (5.7±2.5%) and sham conditions (5.9±2.8%) to single-modality temozolomide (16.9±7.4%) or IMT (28.5±14.9%), and finally to combination treatment with temozolomide and IMT (52.4±21.8%). The results of the quantitative metabolic MTT assay further confirmed the detrimental impact of each treatment modality and the heightened benefits of combined IMT and temozolomide on reducing primary GBM cell viability (FIG. 5B). As stand-alone treatments, IMT (52.2±4.8% viability relative to untreated cells) was significantly more effective than temozolomide (69.7±11.8% viability), as measured by MTT metabolism. The combination of IMT with temozolomide produced further significant GBM cell death compared to either treatment alone (29.1±3.2% viability; FIG. 5B). Comparable effects were produced in immortalized LN229 GBM cells (data not shown).

IMT Enhances the Efficacy of siRNA-Mediated Gene Knockdown in GBM

Figure 6:
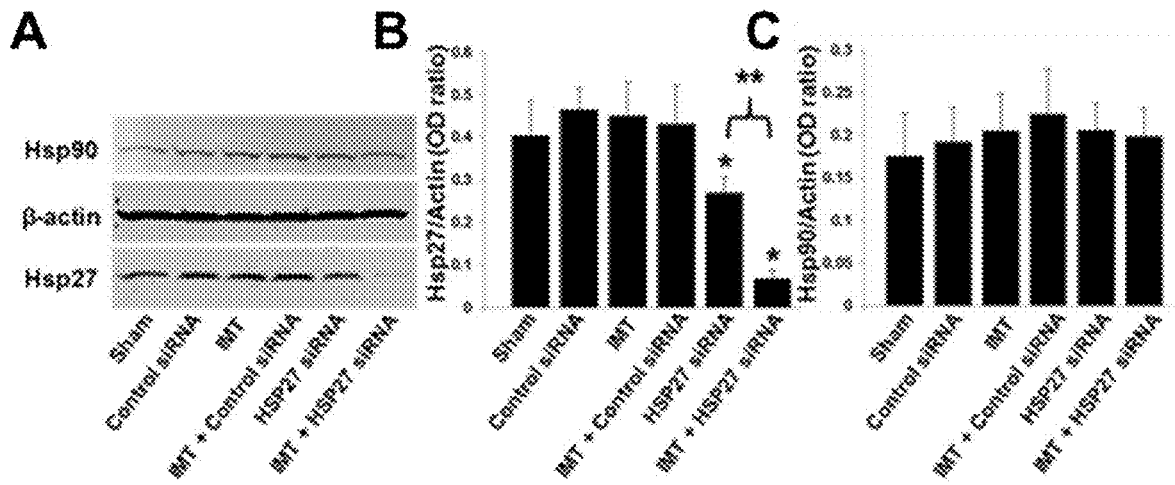
FIG. 6. Panel A: Representative western blot analysis using primary GBM cells derived from an operative tumor specimen. Panels B and C represent mean densitometry values of HSP27 (panel B) and HSP90 (panel C) levels in GBM cells from 3 patients. Values represent mean+standard deviation. Single asterisk indicate a significant difference from the protein expression measured under sham conditions; double asterisk indicates a significant difference in protein expression between the indicated treatment pair (P<0.05, ANOVA). OD, optical density.

Gene silencing methods in primary, patient-derived GBM cells are hindered by poor uptake of hydrophilic genetic material across lipid membranes. This study tested whether IMT may act in concert with HSP27 siRNA, to enhance uptake and bioavailability of siRNA in the cells or through a secondary means of impairing cytokinesis and anti-apoptotic mechanisms. In this example, the pro-tumor chaperone, HSP27, was chosen as the therapeutic target. HSP27 siRNA transfection produced a modest target knockdown that was markedly potentiated with concurrent IMT (FIG. 6 panel A). Sham conditions, IMT and control siRNA were ineffective at reducing HSP27 levels (FIG. 6 panels A-C). Mean densitometry values of FIG. 6 panel B HSP27 and panel C HSP90 levels in GBM cells from 3 patients confirmed the robust and specific knockdown of HSP27 that was significantly enhanced with the co-administration of IMT. HSP90 levels were not notably affected by any of the treatment conditions. Values represent mean plus (+ sign) standard deviation. Single asterisk indicate a significant difference from the protein expression measured under sham conditions; double asterisk indicates a significant difference in protein expression between the indicated treatment pair (P<0.05, ANOVA). OD, optical density.

There was avid expression of HSP27 in patient GBM cells that was not notably affected by control or IMT conditions. In contrast, non-viral transfection of HSP27-specific siRNA (50 nM) using a cationic polymer resulted in a moderate reduction in HSP27 levels that was significantly and consistently enhanced with concomitant IMT (FIG. 6A). Quantitative densitometry of western blot analyses was performed in triplicate using GBM cells obtained from three patients and confirmed no significant change in the level of HSP27 expression among sham-treated cells [0.40±0.08 normalized optical density (OD)], control siRNA-treated (0.46±0.05 OD), IMT-treated (0.45±0.08 OD), or the combination of IMT with control siRNA-treated cells (0.43±0.09 OD). In contrast, GBM cells transfected with HSP27 siRNA alone (0.27±0.04 OD) or the combination of IMT and HSP27 siRNA (0.07±0.02 OD) exhibited significant reductions in HSP27 levels of 32.5% and 82.5%, respectively (FIG. 6B). With either HSP27 siRNA or IMT plus HSP27 siRNA treatment, there was no reduction in the expression of HSP90, a related stress-response chaperones, further supporting the specificity of the gene-targeting method and antitumor impact (FIG. 6C). GBM cell viability in patient specimens was quantified with MTT and, as in the previous series, demonstrated significantly reduced values following IMT alone (60.3±7.7% viability relative to untreated cells). HSP27 siRNA alone also produced significant cytotoxic effects (70.3±5.4% viability). The combination of IMT and control siRNA did not further reduce cell viability compared to IMT alone (57.1±8.8% viability); however, IMT with concomitant HSP27 siRNA produced a robust and significant increase in GBM cell death (35.9±12.8% viability; see also FIG. 7).

IMT-Enhanced Tumoricidal Effect of HSP27 Gene Silencing in GBM Adjuvant

Figure 7:
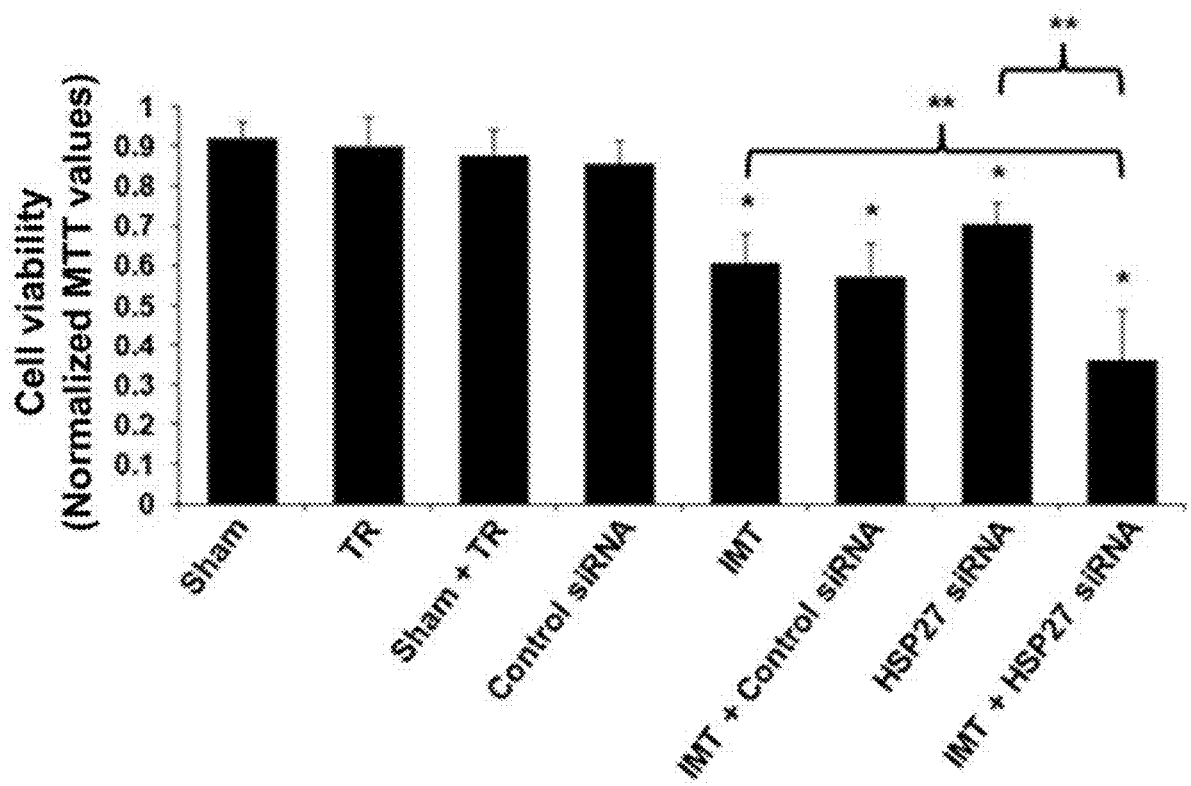
FIG. 7. Histogram illustrating intratumoral modulation therapy (IMT)-enhanced tumoricidal effect of heat-shock protein 27 (HSP27) gene silencing in glioblastoma (GBM). Adjuvant IMT enhanced the tumoricidal effect of targeted HSP27 knockdown in patient GBM cells. Individual measurements show the normalized MTT viability after 48 h of the indicated treatment. IMT alone produced marked loss of GBM viability that was robustly potentiated with HSP27-specific siRNA, but not control siRNA. Significant difference: *from the sham-treated group, **between the indicated treatment pair (p<0.05, ANOVA). Samples were assessed in triplicate using primary GBM cells from three different patients and shown as mean±standard deviation. TR, Transfection reagent.
Figure 8:
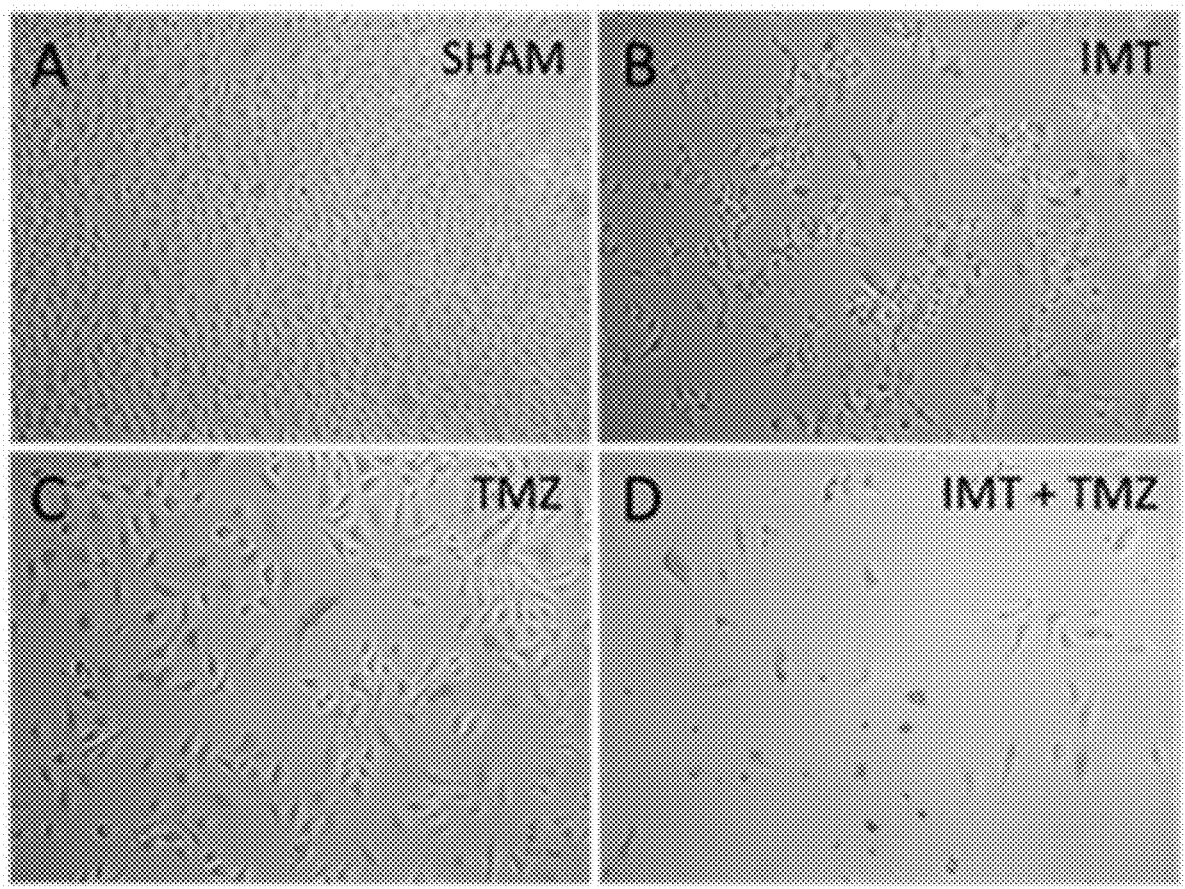
FIG. 8. Panels A-D are photographs of GBM cultures A: sham, B: IMT, C: TMZ and D: IMT+TMZ. IMT with temozolomide (TMZ) potentiates GBM cell death.

With reference to FIG. 7 IMT enhanced the tumoricidal effect of targeted HSP27 knockdown in patient GBM cells. Individual measures show the normalized MTT viability after 48 hours of the indicated treatment. IMT alone produced marked loss of GBM viability that was robustly potentiated with the HSP27-specific siRNA, but not control siRNA. Single asterisks indicate a significant difference from the sham group. The double asterisks of FIG. 7 indicate a significant difference between the indicated treatment pair (P<0.05, ANOVA). Samples were assessed in triplicate using primary GBM cells from 3 different GBM patients and shown as mean+standard deviation. TR, transfection reagent.

Figure 20:
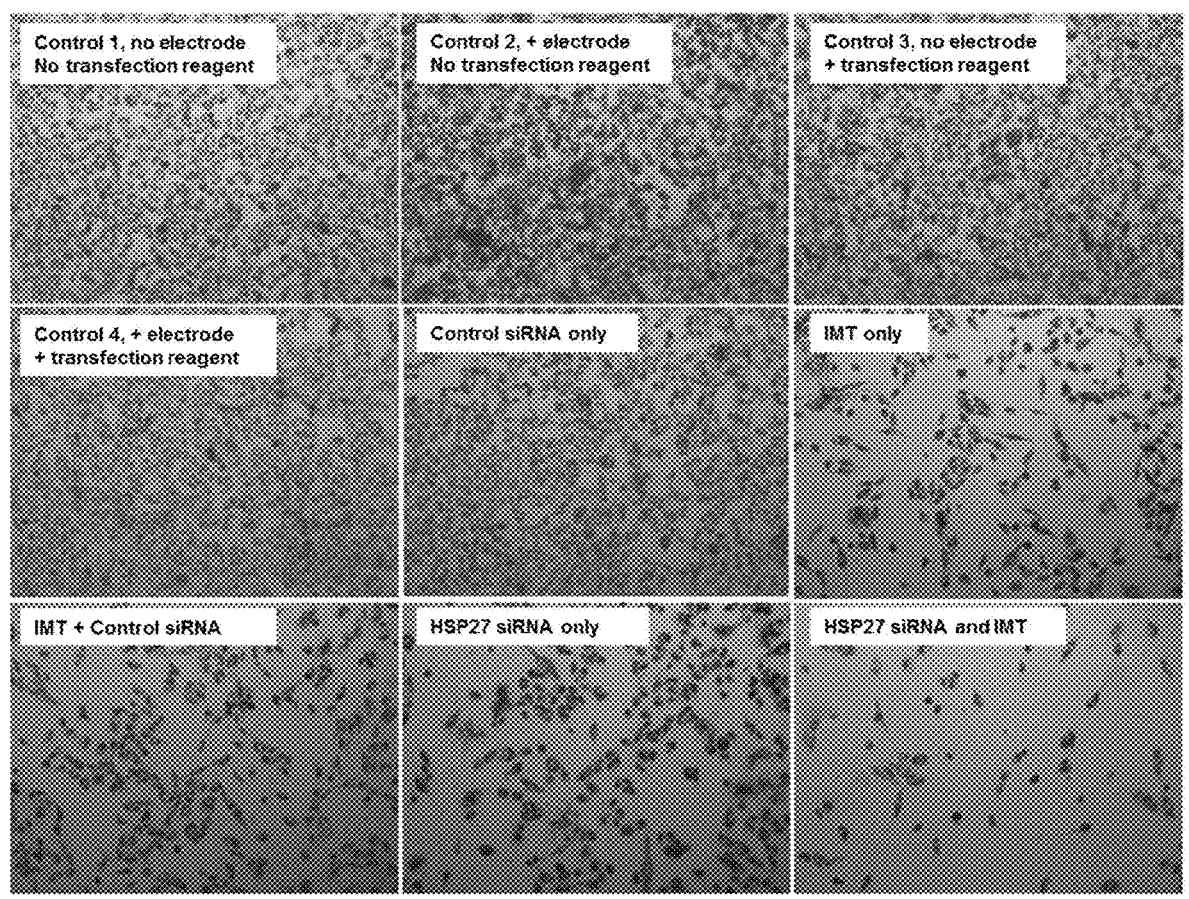
FIG. 20. Photographs of patient-derived GBM cell cultures with various control treatments (panels A-E and G), HSP27 siRNA treatment (panel H), IMT only treatment (panel F) or combination HSP27 siRNA/IMT therapy (panel I). The cells are stained with the blue viability dye, MTT.

With reference to FIG. 20, note the similar density and appearance of the GBM cells under control conditions (panels A-E) but marked loss with either HSP27 siRNA (panel H) or IMT (panel F) alone. This anti-tumor benefit was dramatically potentiated by combining HSP27 siRNA and IMT (panel I).

The example shows the synergistic effect combining IMT and siRNA treatment. The combination of IMT and siRNA is substantially more effective than each treatment taken alone.

Example 2

This example complements the results shown in FIGS. 4-8, 17, 18 and 20, to demonstrate the synergistic enhancement of gene-targeted therapy using high frequency IMT (200 kHz) and synergistic enhancement of high frequency IMT (200 kHz) when combined with TMZ.

High Frequency (200 kHz) IMT Enhances Gene Therapy in GBM

Figure 21:
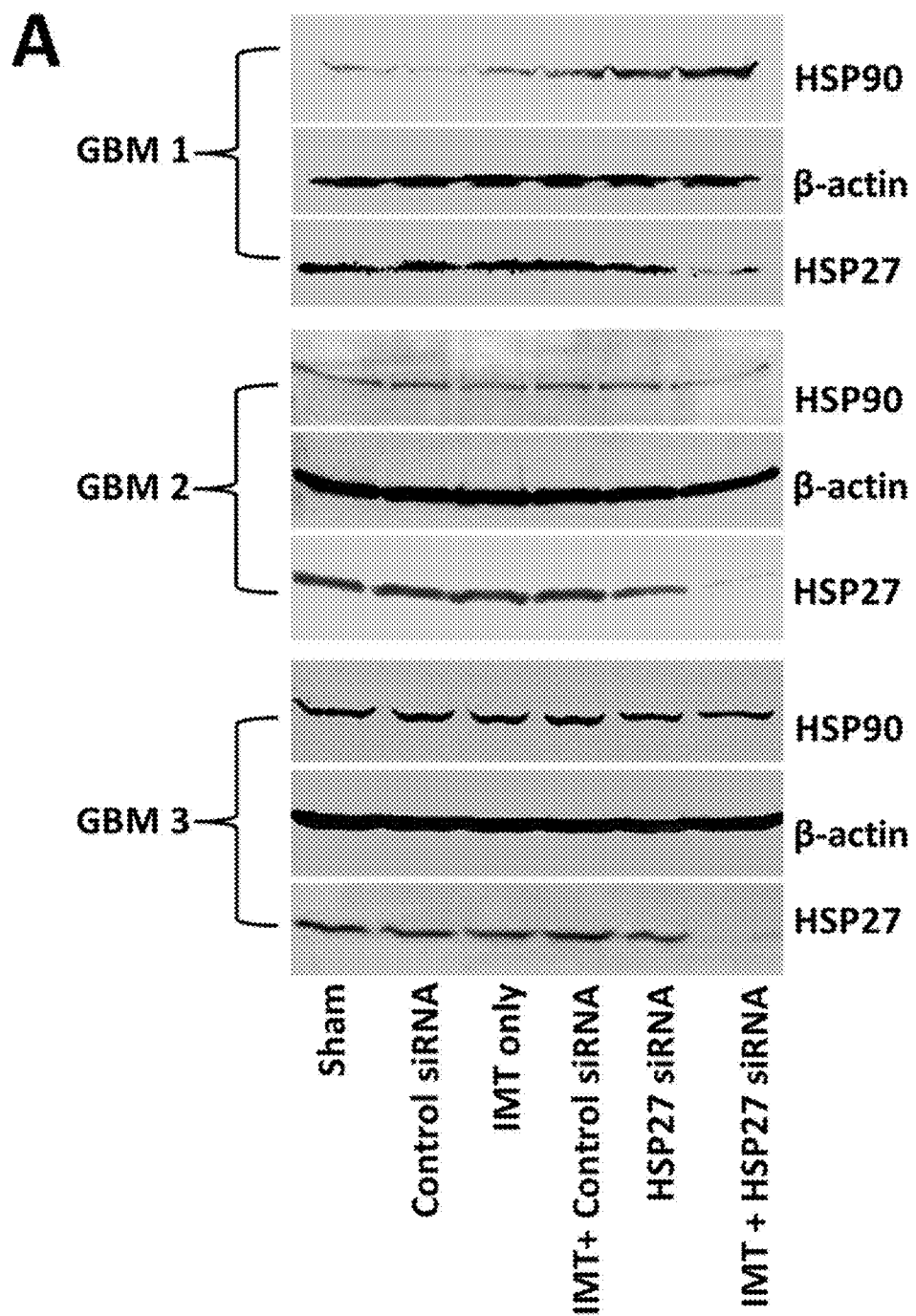
FIG. 21. Panel A: Representative western blot analysis using primary GBM cells derived from 3 operative tumor specimens. HSP27 siRNA transfection produced a modest target knockdown that was markedly potentiated with concurrent IMT. Sham conditions, IMT and control siRNA were ineffective at reducing HSP27 levels. The levels of another tumor-promoting HSP, HSP90, was not affected by the targeted HSP27 and therapies. Panels B and C: Mean densitometry values of HSP27 (B) and HSP90 (C) levels in GBM cells from the 3 patients confirmed the robust and specific knockdown of HSP27 that was significantly enhanced with the co-administration of IMT. HSP90 levels were not notably affected by any of the treatment conditions. Values represent mean+standard deviation. Single asterisk indicate a significant difference from the protein expression measured under sham conditions; double asterisk indicates a significant difference in protein expression between the indicated treatment pair (P<0.05, ANOVA).
Figure 21:
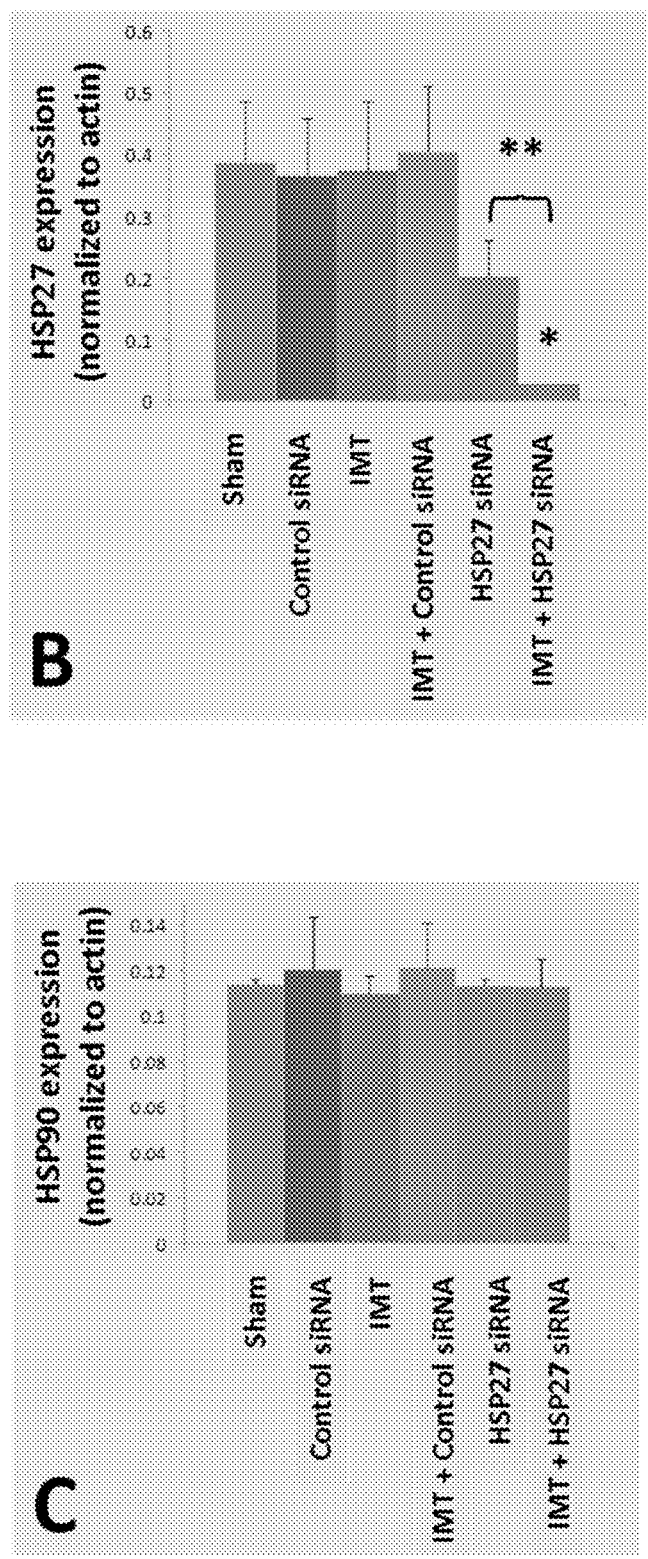

The pro-tumor chaperone, HSP27, was chosen as the therapeutic target. Panel A of FIG. 21 is a representative western blot analysis using primary GBM cells derived from 3 operative tumor specimens. HSP27 siRNA transfection produced a modest target knockdown that was markedly potentiated with concurrent IMT (200 kHz). Sham conditions, IMT and control siRNA were ineffective at reducing HSP27 levels. The levels of another tumor-promoting HSP, HSP90, was not affected by the targeted HSP27 and therapies. Mean densitometry values of FIG. 21B HSP27 and FIG. 21C HSP90 levels in GBM cells from the 3 patients confirmed the robust and specific knockdown of HSP27 that was significantly enhanced with the co-administration of IMT at 200 kHz. HSP90 levels were not notably affected by any of the treatment conditions. Values represent mean+ standard deviation. Single asterisk indicate a significant difference from the protein expression measured under sham conditions; double asterisk indicates a significant difference in protein expression between the indicated treatment pair (P<0.05, ANOVA).

Figure 22:
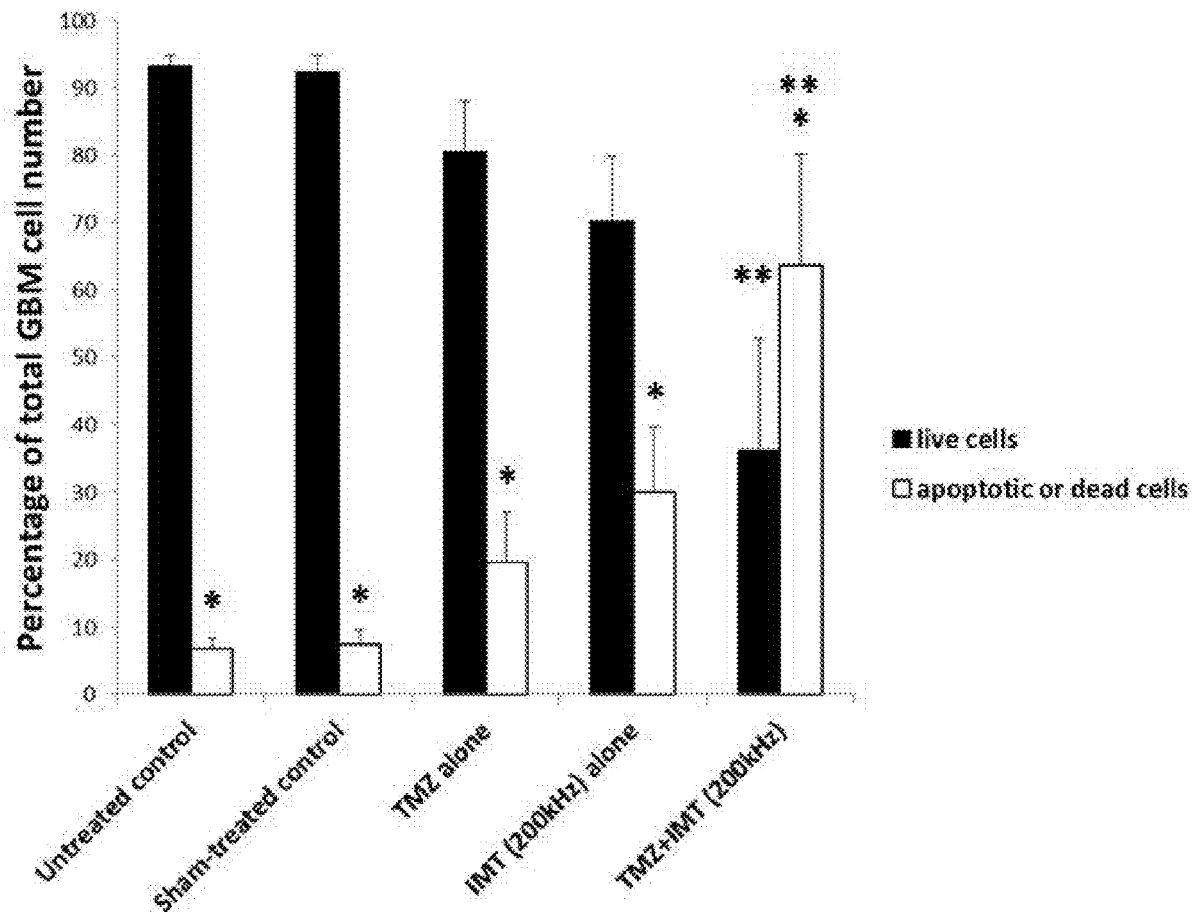
FIG. 22. Flow cytometry data showing the percentage of live and apoptotic/dead GBM cells following the indicated treatments. There was a significant difference between the percentage of live and apoptotic/dead cells within all groups (single asterisk, ANOVA P<0.05). Note, however, that the TMZ+IMT group had reversed major proportions of live and apoptotic/dead cells compared to the other groups. Double asterisks indicate a significant difference between the live or apoptotic/dead fractions and the respective value obtained from untreated cells (P<0.05, ANOVA). Each treatment condition was analyzed in quadruplicate using approximately 30,000 GBM cells per run. The duration of treatment was 72 hours and each measure shown represents the mean+standard deviation for primary GBM cells from 3 patients. TMZ, temozolomide.

Quantitative Effect of High Frequency IMT (200 kHz) Combined with TMZ on Patient GBM Cells FIG. 22 illustrates flow cytometry data showing the percentage of live and apoptotic/dead GBM cells following the indicated treatments. There was a significant difference between the percentage of live and apoptotic/dead cells within all groups (single asterisk, ANOVA P<0.05). Note, however, that the TMZ+IMT group had reversed major proportions of live and apoptotic/dead cells compared to the other groups. Double asterisks indicate a significant difference between the live or apoptotic/dead fractions and the respective value obtained from untreated cells (P<0.05, ANOVA). Each treatment condition was analyzed in quadruplicate using approximately 30,000 GBM cells per run. The duration of treatment was 72 hours and each measure shown represents the mean+standard deviation for primary GBM cells from 3 patients. TMZ, temozolomide Example 3—In Vivo IMT Model The F98 rat GBM model is used in this study. Briefly, F98 cells are derived from an anaplastic glioma in a Fischer rat and produce treatment-resistant brain tumors with GBM properties when implanted into syngeneic host brains (21). Adult male rats undergo stereotactic implantation of a commercial cannula/electrode combination bilaterally into the striatum. This MRI-compatible device permits infusion of the F98 cells and siRNA, with concurrent IMT, at the epicenter of the growing tumor. A reference electrode is tunneled through the nuchal skin for easy access. The IMT cables are suspended via a commutator, so that the animal can move freely within its home cage during treatment (see FIG. 10).

Adult Fischer rats underwent stereotactic implantation of F98 GBM tumor cells into bilateral striata. After 4 days of tumor growth in the brain, one side was treated for 7 days using IMT with a frequency of 200 kHz and amplitude of +/−2V. The contralateral tumor was fitted with electrode hardware but did not receive treatment (i.e., sham). Shown in FIGS. 10A and 10C is a representative animal receiving IMT in its home cage. With reference to FIG. 10, the therapy is delivered using a waveform generator 801 connected to an indwelling brain electrode via a commutator 802 that allows free movement of the animal at all times. Cannula electrode constructs 803 were implanted bilaterally into the striatum. Only the treated tumor received IMT; the other side had the same hardware implanted but was not treated. The construct 803 consists of a brain cannula 804 through which the F98 cells were implanted (dashed arrow) and adjacent brain electrode 805 to deliver IMT within the epicenter of the GBM field (short solid arrow). There is a reference electrode 806 (long solid arrow) that is implanted in the nucchal soft tissues. The reference electrode is not restricted to the nuchal soft tissues, and it may also be implanted in other places, such as the subgaleal or subdural spaces, or other areas appropriate for tumor treatment. FIG. 10C is a closer view of the subject undergoing IMT. Animals showed no evidence of ongoing discomfort, medical complications, neurological deficits or seizures during the therapy.

IMT Reduces Overall Brain Tumor Mass

FIG. 11 are photographs of an extracted rat brain that housed bilateral GBM tumors in the striatum. IMT implants had been placed bilaterally (now removed) but only activated on the right side. Note the IMT-mediated reduction in hemispheric volume on the right compared to the left. The image shown in panel B of FIG. 11 shows the same brain of panel A of FIG. 11 with an overlaid grid for size calibration.

In Vivo Bioluminescence Imaging (BLI) in the F98 GBM Model

Figure 12:
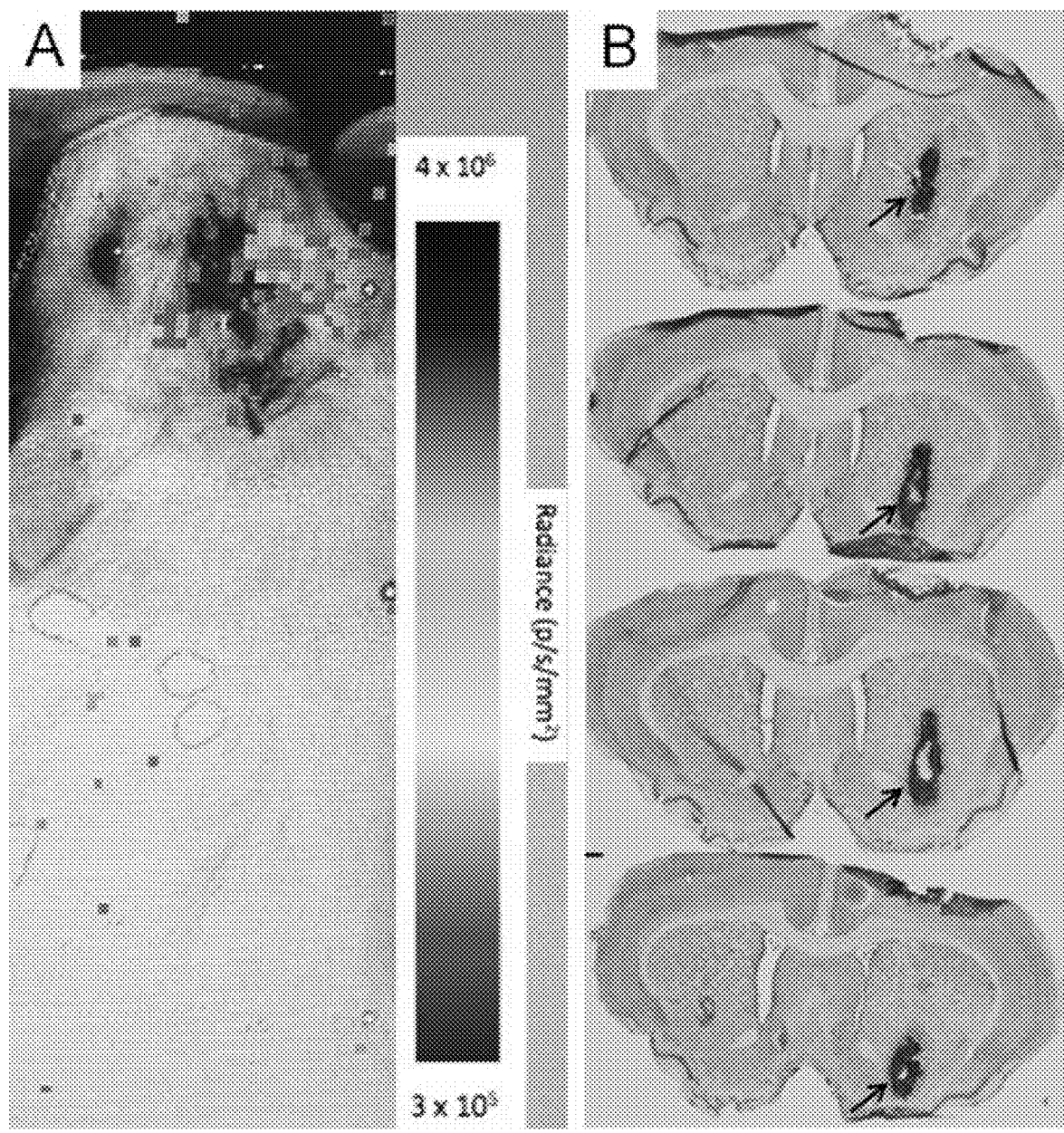
FIG. 12. A: In vivo bioluminescence imaging (BLI) of F98 GBM cells transduced to stably express Firefly luciferase implanted into the striatum of a Fischer rat. B: rostral (top) to caudal hematoxylin-stained brain sections through the tumor (arrows) of the rat of panel A. These data were obtained 4 days after implanting a striatal deposit of 2 µl DMEM containing 40,000 F98 GBM cells and demonstrate the aggressive tumorigenesis produced in this model.

F98 GBM cells transduced to stably express Firefly luciferase were implanted into the striatum of a Fischer rat. FIGS. 12 A shows BLI tumor signal and 12 B rostral (top) to caudal hematoxylin-stained brain sections through the tumor (arrows). These data were obtained 4 days after implanting a striatal deposit of 2 µl DMEM containing 40,000 F98 GBM cells and demonstrate the aggressive tumorigenesis produced in this model.

Figure 13:
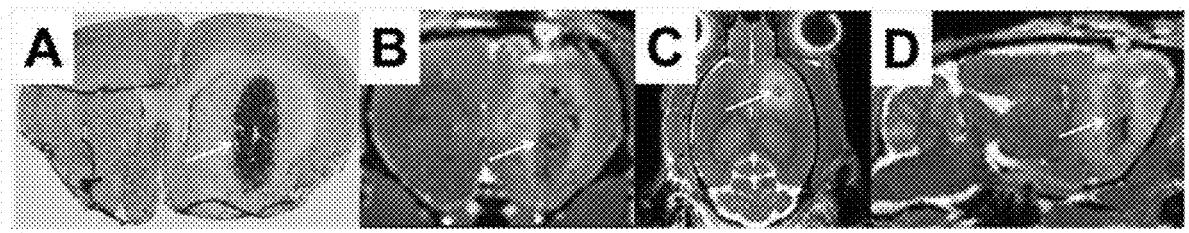
FIG. 13. A: photograph of a hematoxylin-stained brain section through a striatal F98 GBM tumor (arrow) in a Fischer rat and the corresponding coronal (B), axial (C) and sagittal (D) T2-weighted MR images of the tumor (arrows) taken prior to sacrifice and brain retrieval.

The T2-weighted MRI shown in FIGS. 13 B-D provides accurate 3-dimensional delineation of the tumor (arrows), suitable for volumetric analysis, and associated cerebral edema evident as brighter signal around the tumor. The MRI studies complement the BLI and immunohistology to evaluate tumor response to IMT in this project.

Anti-Tumor Effects of IMT In Vivo

Figure 14:
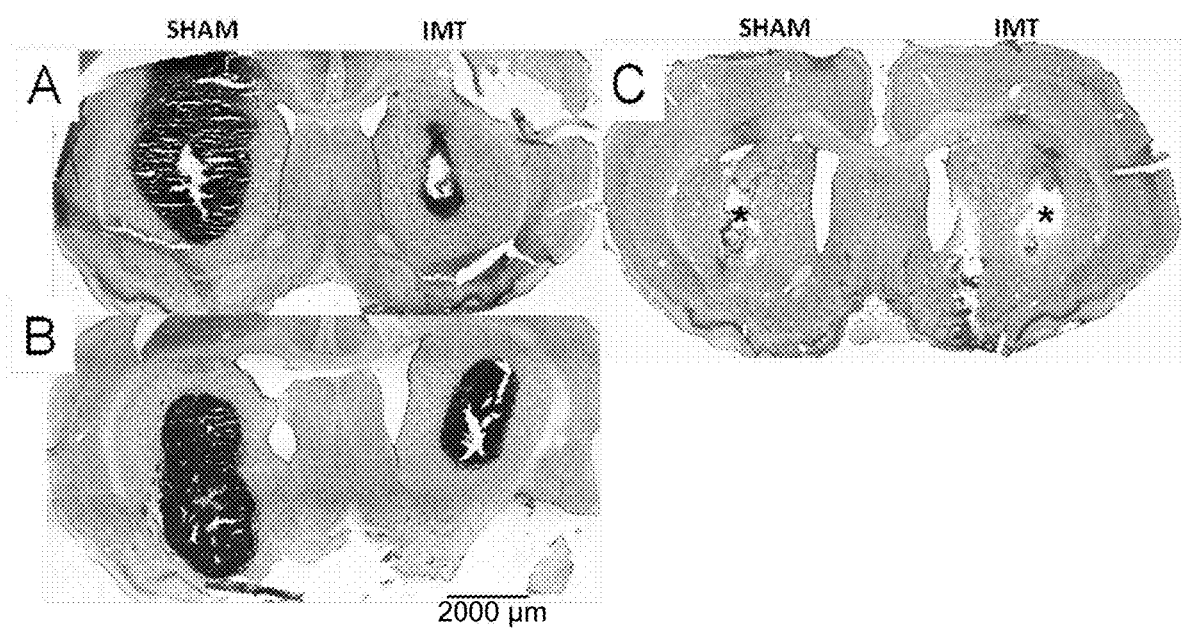
FIG. 14. Images through the brains of adult Fischer rats treated with sham conditions (i.e., no stimulation) or IMT for 7 days (200 kHz, +/−2V). Panels A and B show distinct 11-day old tumors after the indicated treatment. The tumor in Panel A was treated using an insulated electrode that did not emit current but rather established a localized electric field. The tumor in Panel B was treated with an uninsulated electrode to deliver electrical current to the GBM. Panel C: Image through the brain of a control animal with implanted bilateral IMT constructs, but no tumor cells. Asterisks indicate the hardware defect noted in all sham and treated tissues. No overt injury was produced in normal brain tissue by IMT. IMT appears to selectively target dividing neoplastic cells. The scale bar in panel B applies to panels A and C as well.

FIG. 14 includes representative images through the brains of adult Fischer rats treated with sham conditions (i.e., no stimulation) or IMT for 7 days (200 kHz, +/−2V). The IMT treatment was initiated 4 days after injecting 2 µl DMEM containing 40,000 F98 GBM cells into bilateral striata.

Panels A and B of FIG. 14 therefore show an 11-day old tumor after the indicated treatment. Panels A and B of FIG. 14 are two example of brains housing bilateral GBM tumors with IMT or sham conditions delivered for 1 week. Electrodes used in panel A were insulated with Entellan®. Electrodes used in panel B were uninsulated. Note the dramatic attenuation of the treated tumor relative to the sham control tumor, with IMT effectively reducing the growth and spread of the GBM cells through the brain. Panel C of FIG. 14, which represents control animals with implanted bilateral IMT constructs, but no tumor cells, revealed that IMT does not produce notable injury to normal brain tissue relative to the sham control conditions. Asterisks in FIG. 14C indicate the hardware defect noted in all sham and treated tissues. The scale bar in B applies to panels A-C of FIG. 14.

Therapeutic Benefit of IMT In Vivo

Figure 15:
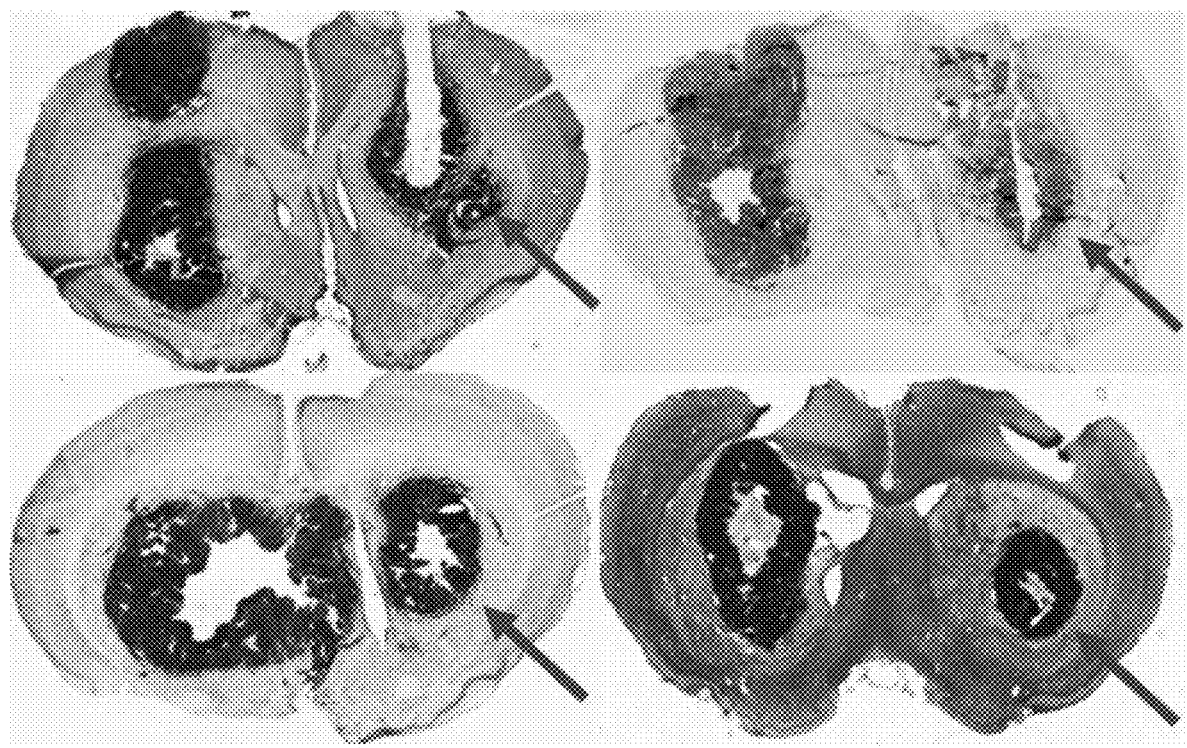
FIG. 15. Panels A-D: images of brain sections through bilateral GBM tumors in four additional Fischer rats. The IMT hardware was implanted on both sides but activated only on the side indicated by the arrow. The IMT-treated tumors in these animals were markedly smaller than in the sham-treated controls.

FIG. 15 panels A-D shown brain sections through bilateral GBM tumors in four additional Fischer rats. The IMT hardware was implanted on both sides but activated only on the side indicated by the arrow. The IMT-treated tumors in these four additional animals were markedly smaller than in the sham-treated controls.

Figure 16:
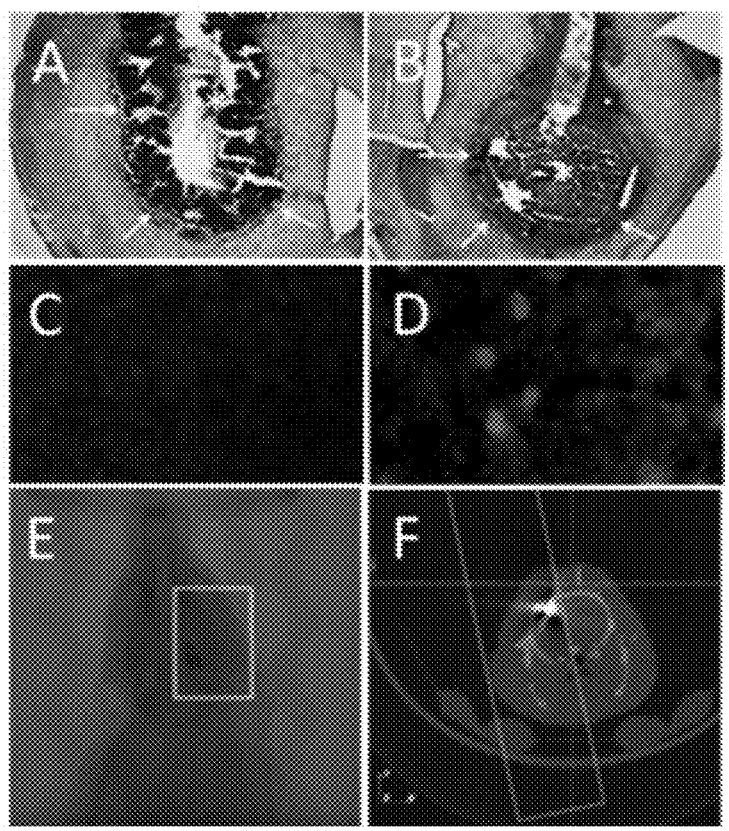
FIG. 16. In vivo F98 GBM model Electrodes were implanted and GBM tumors grown bilaterally in the Fischer rat striata. A: The left side of rat striata was sham (i.e., no stimulation). B: IMT treatment on the right side of rat striata. C: caspase-3 activation (stains red) on the sham side (no red stain is seen). D: capsase-3 activation (stains red) on the IMT-treated tumor side. E: The CT scout view shows another rat with a unilateral electrode in a F98 GBM tumor being prepared for radiotherapy. F: photograph of a radiation dosing plan that can be used in combination with IMT to treat the GBM tumor.
Figure 17:
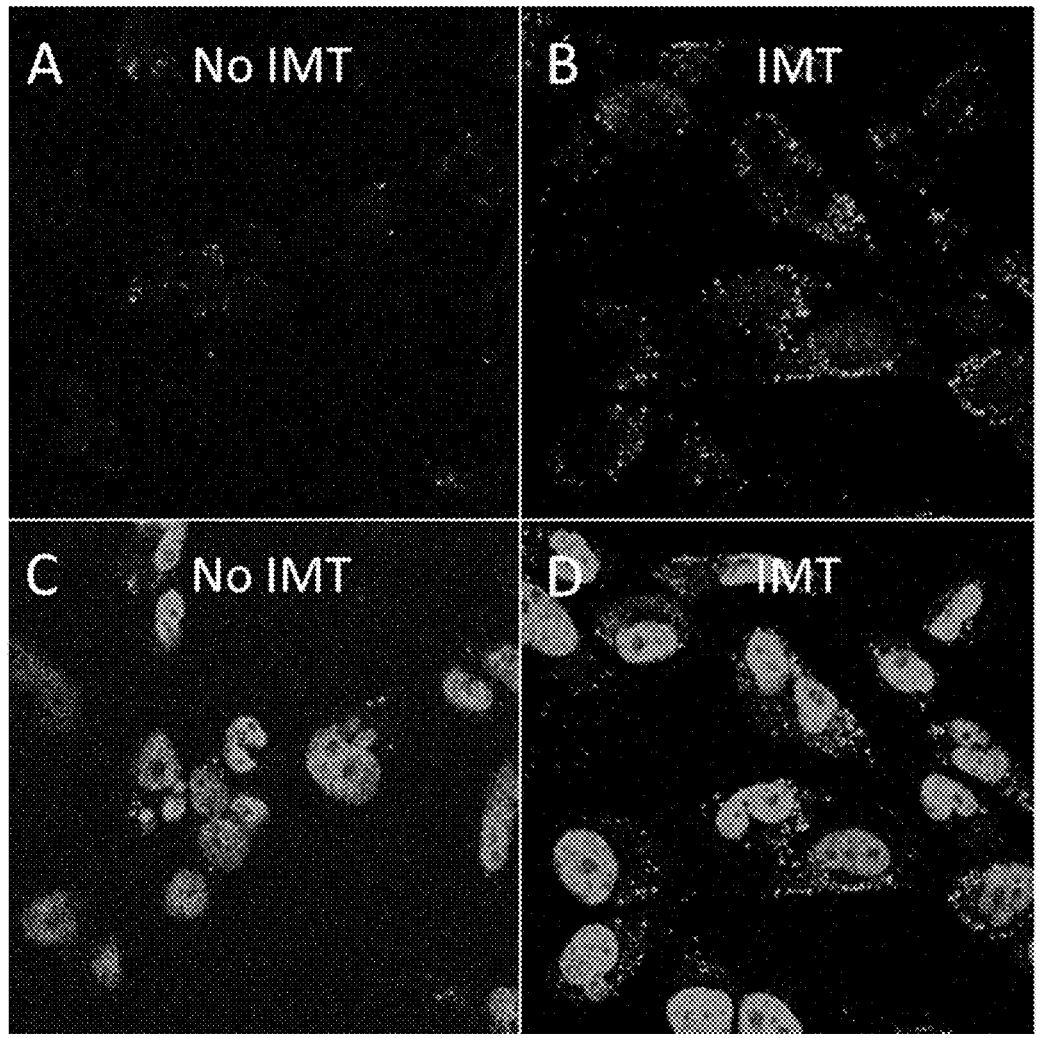
FIG. 17. IMT enhances siRNA uptake in patient GBM cells. A-D: Confocal microscopy photographs showing 48-hour, fluorescent-labeled siRNA transfection using conventional lipid-based methods in the absence (A, C) and presence (B, D) of IMT. Note the dramatic increase in siRNA signal in GBM cells concurrently receiving IMT. The lower panels show the respective images above, with DAPI nuclear stain overlay.
Figure 18:
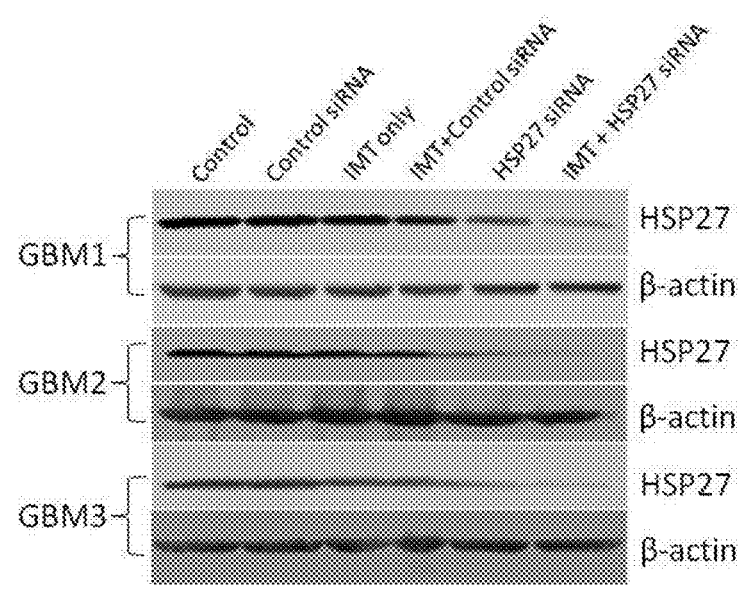
FIG. 18. IMT enhances targeted gene silencing in patient GBM cells. Western blot analysis from primary GBM cells derived from 3 patient tumors (GBM1, GBM2 and GBM3). HSP27 siRNA 48-hour transfection produced a modest target knockdown in primary GBM cells that was markedly potentiated with concurrent IMT. No reduction in HSP27 was observed with control siRNA without or with IMT, and non-target HSP90 expression was unchanged with any of the treatments (not shown), indicating target specificity of IMT-siRNA treatment.

With reference to FIG. 16 in vivo F98 GBM model Electrodes were implanted and GBM tumors grown bilaterally in the Fischer rat striata. The left side was sham (i.e., no stimulation) and showed robust tumor growth (marked by arrows in FIG. 16A). Conversely, IMT on the right side produced a marked reduction in tumor volume (arrows, FIG. 16B). Scant caspase-3 activation (stains red) occurred on the sham side (FIG. 16C), whereas the IMT-treated tumor was robustly red labeled (FIG. 16D). The CT scout view shows another rat with a unilateral electrode in a F98 GBM tumor being prepared for radiotherapy (FIG. 16E). Radiation dosing plan that can be used in combination with IMT to treat the GBM tumor is illustrated in FIG. 16F.

Example 4—Mechanism of IMT-Enhanced Transfection

Figure 19:
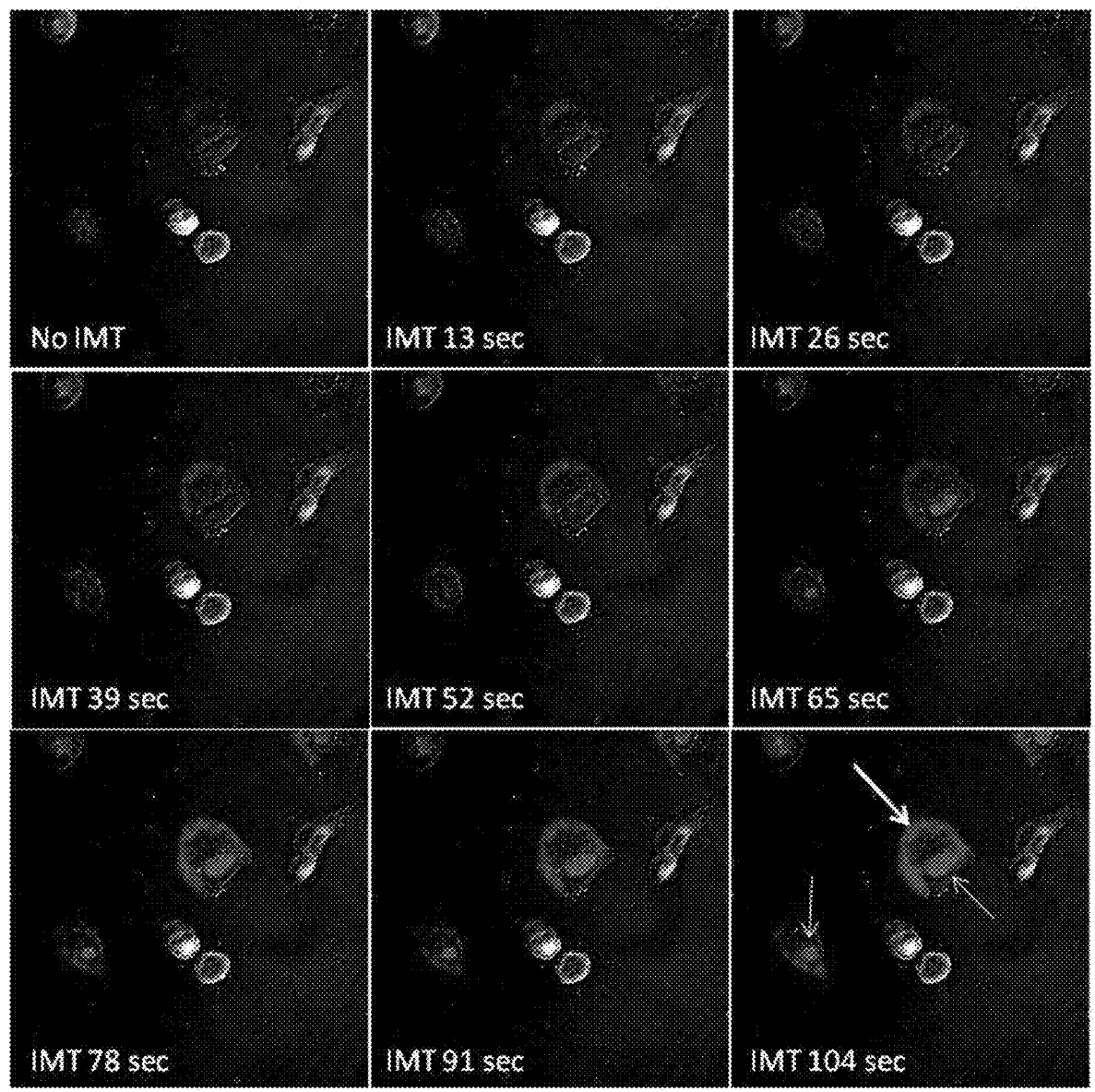
FIG. 19. IMT improves uptake of cell impermeable substances in GBM cells. Time lapse video fluoroscopic images of live patient GBM cells in culture medium containing the membrane impermeant dye, propidium iodide (PI; red fluorescence).

The in vitro and in vivo studies show that GBM cells treated with IMT undergo caspase-activated apoptosis, however membrane disruption was also evident by the cellular uptake of impermeable dyes (FIGS. 3 and 16). These findings may reflect necrotic death, membrane degeneration after apoptosis, or facilitated dye uptake through endocytosis, electrophoresis or electroporation. To address this question, primary patient GBM cells were treated with IMT and subjected to the investigations below. Live cell imaging: These studies evaluate acute changes in membrane integrity in live GBM cells exposed to IMT. Cells are imaged for 1-3 hours under sham or IMT conditions, using an Olympus FluoView™ FV1000 confocal microscope for evidence of IMT-mediated uptake of propidium iodide, a membrane-impermeable fluorescent molecule (FIG. 19). Panel A of FIG. 19: no IMT, Panels B-I of FIG. 19: IMT after 13, 26, 39, 52, 65, 78, 91 and 104 seconds respectively.

With reference to FIG. 19, at baseline (panel A, i.e., no IMT), there is no substantial fluorescent signal from the cells; with uptake seen only in the occasional degenerating cell, as is normal under culture conditions. As IMT (+/−2V AC, 200 kHz) is initiated, there is slow, progressive enhancement of the signal emanating from nuclear (small narrow arrows in panel I of FIG. 19) and cytoplasmic (large bolded arrow in panel I of FIG. 19) compartments of the GBM cells. The images of FIG. 19 illustrate that IMT increases cellular uptake of membrane impermeable agents through nuclear and cytoplasmic envelopes.

Example 5—In Vivo IMT-Enhanced Transfection Using the F98 GBM Model

These experiments evaluate the in vivo efficacy of IMT-mediated transfection, with and without standard chemoradiation. Continuous IMT is initiated 1 week following surgery as described before. Seven animal groups (10 animals/group) are used for both low and high frequency IMT stimulation parameters, with bilateral striatal GBM; one side used for sham control. The group size is chosen to adequately temper inter-animal variability, with potential loss due to unexpected problems/deaths, and be completed within the 3 year study window. IMT is performed alone (group 1), with single agent siRNA targeting HSP27 or HSP70 (groups 2, 3), with dual siRNA therapy (group 4), or with the prior siRNA options and chemoradiation treatment (groups 5-7). siRNA (50 nM in 2 μl PBS) is delivered through the cannula 803 shown in FIG. 10B on day 1 and day 4 of IMT treatment. Dual siRNA therapy use a total volume of 2 μl, with each siRNA concentration adjusted to 50 nM. Temozolomide (TMZ) dosing was 18 mg/kg i.p., the clinical equivalent of 200 mg/m2/day (24-25); the radiation dose is 30 Gy in 2 fractions. F98 cells respond to in vitro radiation doses between 12-18 Gy (26) and radiation necrosis occurs in F98 models using 60 Gy (27). The in vivo RT dose in this study falls between these values to induce anti-tumor effect without radiation necrosis. Cranial imaging is performed using a 9.4T MRI system immediately prior to, and following, the treatment course. Animals are euthanized at the end of the treatment period or earlier if there are signs of severe neurological compromise. Brains are sectioned for histological staining and immunocytochemistry. Volumetric tumor dimensions are quantified, and indices of proliferation (MIB1), apoptosis (activated caspase-3 and TUNEL) and HSP27/70 expression are assessed. A small number of animals (N=5) is used to evaluate the in vivo distribution of a fluorescent-labeled control siRNA delivered to the tumor in the absence and presence of IMT.

Determining the mechanisms of IMT-induced cell death and IMT-enhanced transfection in GBM allows to maximally exploit these effects before translating to the clinical settings.

Figure 23:
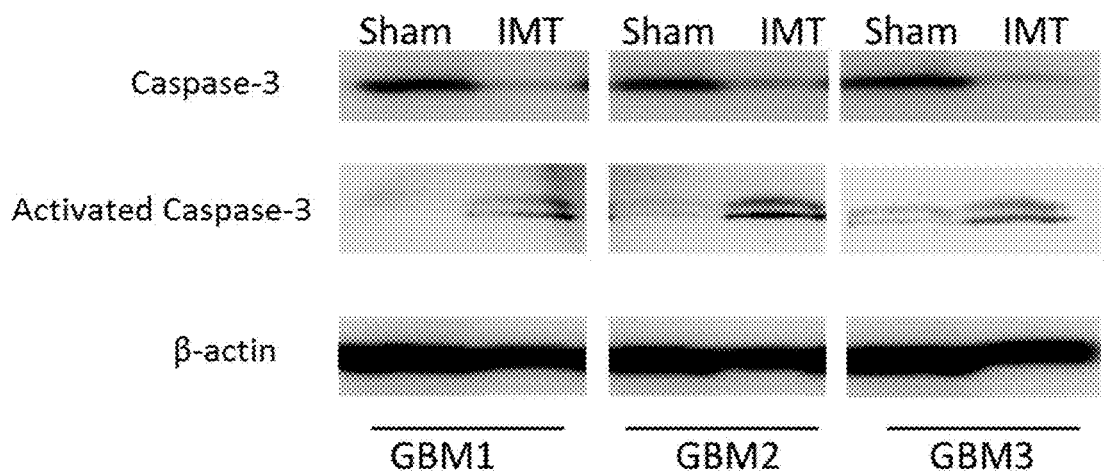
FIG. 23. High frequency (200 kHz) IMT activates caspase-3 in GBM cells. Shown are Western blot studies from 3 patient-derived GBM cell preparations treated with 72 hours of sham or IMT (+/−2V, 200 kHz) conditions. The levels of intact caspase-3 are markedly reduced and correspond to an increase in the activated (cleaved) form, indicative of apoptosis induction, during IMT.

High frequency (200 kHz) IMT activates caspase-3 in GBM cells. Shown in FIG. 23 are Western blot studies from 3 patient-derived GBM cell preparations treated with 72 hours of sham or IMT (+/−2V, 200 kHz) conditions. The levels of intact caspase-3 are markedly reduced and correspond to an increase in the activated (cleaved) form, indicative of apoptosis induction, during IMT.

The above disclosure generally describes the present invention. Changes in form and substitution of equivalents are contemplated as circumstances may suggest or render expedient. Although specific terms have been employed herein, such terms are intended in a descriptive sense and not for purposes of limitation. Other variations and modifications of the invention are possible. As such modifications or variations are believed to be within the sphere and scope of the invention as defined by the claims appended hereto.

REFERENCES

1. Cavenee W K, Louis D N, Ohgaki H. WHO Classification of Tumours of the Central Nervous System. WHO Publications Fourth edition, 2007.

2. Orlowski, S.; Belehradek, J.; Paoletti, C.; Mir, L. M. Transient electropermeabilization of cells in culture. Increase of the cytotoxicity of anticancer drugs. Biochem. Pharmacol. 37:4727-4733; 1988.
3. Zimmermann U. Electric field-mediated fusion and related electrical phenomena. Biochim Biophys Acta. 1982 Nov. 30; 694(3):227-77.
4. Horikoshi T, Naganuma H, Ohashi Y, Ueno T, Nukui H. Enhancing effect of electric stimulation on cytotoxicity of anticancer agents against rat and human glioma cells. Brain Res Bull. 2000 Mar. 15; 51(5):371-8.
5. Salford L G, Persson B R, Brun A, Ceberg C P, Kongstad P C, Mir L M. A new brain tumour therapy combining bleomycin with in vivo electropermeabilization. Biochem Biophys Res Commun. 1993 Jul. 30, 194(2):938-43
6. Pudenz, R. Adverse effects of electrical energy applied to the nervous system. Neurosurgery 1:190-191; 1977.
7. Kirson E D, Dbalý, Tovarys F, Vymazal J, Soustiel J F, Itzhaki A, Mordechovich D, Steinberg-Shapira S, Gurvich Z, Schneiderman R, Wasserman Y, Salzberg M, Ryffel B, Goldsher D, Dekel E, Palti Y. Alternating electric fields arrest cell proliferation in animal tumor models and human brain tumors. Proc Natl Acad Sci USA. 2007 Jun. 12; 104(24):10152-7. Epub 2007 Jun. 5.
8. Pless M, Weinberg U. Tumor treating fields: concept, evidence and future. Expert Opin Investig Drugs. 2011 August; 20(8):1099-106. doi: 10.1517/13543784.2011.583236. Epub 2011 May 9.
9. Stupp R, Wong E T, Kanner A A, Steinberg D, Engelhard H, Heidecke V, Kirson E D, Taillibert S, Liebermann F, Dbalaý, Ram Z, Villano J L, Rainov N, Weinberg U, Schiff D, Kunschner L, Raizer J, Honnorat J, Sloan A, Malkin M, Landolfi J C, Payer F, Mehdorn M, Weil R J, Pannullo S C, Westphal M, Smrcka M, Chin L, Kostron H, Hofer S, Bruce J, Cosgrove R, Paleologous N, Palti Y, Gutin P H. NovoTTF-100A versus physician's choice chemotherapy in recurrent glioblastoma: A randomised phase III trial of a novel treatment modality. Eur J Cancer. 2012 September; 48(14):2192-202. Epub 2012 May 18.
10. Kanner A A, Wong E T, Villano J L, Ram Z; EF-11 Investigators. Post Hoc analyses of intention-to-treat population in phase Ill comparison of NovoTTF-100A™ system versus best physician's choice chemotherapy. Semin Oncol. 2014 October; 41 Suppl 6:S25-34.
11. Deniau J M, Degos B, Bosch C, Maurice N. Deep brain stimulation mechanisms: beyond the concept of local functional inhibition. Eur J Neurosci. 2010 October; 32(7):1080-91. doi: 10.1111/j.1460-9568.2010.07413.x.
12. Wang J, Lu Z, Wientjes M G, Au J L. Delivery of siRNA therapeutics: barriers and carriers. AAPS J. 2010 December; 12(4):492-503.
13. Mossop B J, Barr R C, Henshaw J W, Zaharoff D A, Yuan F. Electric fields in tumors exposed to external voltage sources: implication for electric field-mediated drug and gene delivery. Ann Biomed Eng. 2006 October; 34(10): 1564-72.
14. Tang L, Yao C, Sun C. Apoptosis induction with electric pulses—a new approach to cancer therapy with drug free. Biochem Biophys Res Commun. 2009 Dec. 25; 390(4): 1098-101.
15. Acunzo J, Andrieu C, Baylot V, So A, Rocchi P. Hsp27 as a therapeutic target in cancers. Curr Drug Targets. 2014 April; 15(4):423-31.
16. Lianos G D, Alexiou G A, Mangano A, Mangano A, Rausei S, Boni L, Dionigi G, Roukos D H. The role of heat shock proteins in cancer. Cancer Lett. 2015 May 1; 360(2):114-8.
17. Yang I, Fang S, Parsa A T. Heat shock proteins in glioblastomas. Neurosurg Clin N Am. 2010 January; 21(1):111-23.
18. Belkacemi L, Hebb M O. HSP27 knockdown produces synergistic induction of apoptosis by HSP90 and kinase inhibitors in glioblastoma multiforme. Anticancer Res. 2014 September; 34(9):4915-27.
19. Aloy M T, Hadchity E, Bionda C, Diaz-Latoud C, Claude L, Rousson R, Arrigo A P, Rodriguez-Lafrasse C. Protective role of Hsp27 protein against gamma radiation-induced apoptosis and radiosensitization effects of Hsp27 gene silencing in different human tumor cells. Int J Radiat Oncol Biol Phys. 2008 Feb. 1; 70(2):543-53.
20. Jakubowicz-Gil J, Langner E, Bdziul D, Wertel I, Rzeski W. Silencing of Hsp27 and Hsp72 in glioma cells as a tool for programmed cell death induction upon temozolomide and quercetin treatment. Toxicol Appl Pharmacol. 2013 Dec. 15; 273(3):580-9.
21. Mathieu D, Lecomte R, Tsanaclis A M, Larouche A, Fortin D. Standardization and detailed characterization of the syngeneic Fischer/F98 glioma model. Can J Neurol Sci. 2007 August; 34(3):296-306.
22. Beaman G M, Dennison S R, Chatfield L K, Phoenix D A. Reliability of HSP70 (HSPA) expression as a prognostic marker in glioma. Mol Cell Biochem. 2014 August; 393(1-2):301-7.
23. Wang X, Chen M, Zhou J, Zhang X. HSP27, 70 and 90, anti-apoptotic proteins, in clinical cancer therapy (Review). Int J Oncol. 2014 July; 45(1):18-30.
24. Ostermann S, Csajka C, Buclin T, Leyvraz S, Lejeune F, Decosterd L A, Stupp R. Plasma and cerebrospinal fluid population pharmacokinetics of temozolomide in malignant glioma patients. Clin Cancer Res. 2004 Jun. 1; 10(11):3728-36.
25. Zhou Q, Guo P, Wang X, Nuthalapati S, Gallo J M. Preclinical pharmacokinetic and pharmacodynamic evaluation of metronomic and conventional temozolomide dosing regimens. J Pharmacol Exp Ther. 2007 April; 321(1):265-75.
26. Gil S, Sarun S, Biete A, Prezado Y, Sabés M. Survival analysis of F98 glioma rat cells following minibeam or broad-beam synchrotron radiation therapy. Radiat Oncol. 2011 Apr. 13; 6:37.
27. Bolcaen J, Descamps B, Deblaere K, Boterberg T, De Vos Pharm F, Kalala J P, Van den Broecke C, Decrock E, Leybaert L, Vanhove C, Goethals I. (18)F-fluoromethyl-choline (FCho), (18)Ffluoroethyltyrosine (FET), and (18) F-fluorodeoxyglucose (FDG) for the discrimination between highgrade glioma and radiation necrosis in rats: a PET study. Nucl Med Biol. 2015 January; 42(1):38-45.
28. Lacouture M E, Davis M E, Elzinga G, Butowski N, Tran D, Villano J L, DiMeglio L, Davies A M, Wong E T. Characterization and management of dermatologic adverse events with the NovoTTF-100A System, a novel anti-mitotic electric field device for the treatment of recurrent glioblastoma. Semin Oncol. 2014 June; 41 Suppl 4:S1-14. doi: 10.1053.
29. Stupp R, Taillibert S, Kanner A A, Kesari S, Steinberg D M, Toms S A, Taylor L P, Lieberman F, Silvani A, Fink K L, Barnett G H, Zhu J J, Henson J W, Engelhard H H, Chen T C, Tran D D, Sroubek J, Tran N D, Hottinger A F, Landolfi J, Desai R, Caroli M, Kew Y, Honnorat J, ldbaih A, Kirson E D, Weinberg U, Palti Y, Hegi M E, Ram Z. Maintenance Therapy With Tumor-Treating Fields Plus Temozolomide vs Temozolomide Alone for Glioblastoma: A Randomized Clinical Trial. JAMA. 2015 Dec. 15; 314(23):2535-43. doi: 10.1001

30. Garcia P A, Pancotto T, Rossmeisl J H Jr, Henao-Guerrero N, Gustafson N R, Daniel G B, Robertson J L, Ellis T L, Davalos R V. Non-thermal irreversible electroporation (N-TIRE) and adjuvant fractionated radiotherapeutic multimodal therapy for intracranial malignant glioma in a canine patient. Technol Cancer Res Treat. 2011 February; 10(1):73-83.

The invention claimed is:

1. An intratumoral modulation therapy (IMT) method for reversing, minimizing, alleviating, or substantially inhibiting the progress or treatment resistance of a tumor in the central nervous system (CNS) in a patient in need, and preventing recurrence of the tumor in the CNS in the patient in need comprising:
    (a) chronically and surgically implanting in the patient in need at least one electrode that delivers an electric current or an electric field in a site, the site being selected from (i) a site adjacent to the tumor, (ii) a site within the tumor, or (iii) a site of the CNS suspected of having tumor cells, the at least one electrode having electrical leads connected thereto; and
    (b) generating the electric current or electric field having a combination of electrical parameters that preferentially targets neoplastic cells, and permanently and invasively applying to the site the electric current or electric field having said combination of electrical parameters through the electrical leads to the electrode chronically implanted in the site to provide permanently active therapy to the patient in need,
    wherein the electric current or electric field is alternating current or alternating electric field, and wherein the combination of electrical parameters include voltage of about 10 V or under at a frequency of 50 Hz to 500 kHz or voltage of about +/−10 V or under at a frequency of 50 Hz to 500 kHz, or voltage of about +/−10 V or under at a frequency of 50-200 Hz.

2. The method of claim 1, wherein the method further comprises delivering a therapeutic agent to the site during the chronically and invasively applying of the electric current or electric field, the therapeutic agent being selected from a chemotherapeutic agent, a genetic material, radiation or a combination thereof, wherein a combined effect on the tumor treatment of the electric stimulation and therapeutic agent is substantially greater than the effect of each the electric stimulation, and the therapeutic agent taken alone.

3. The method of claim 2, wherein the therapeutic agent is a genetic material associated with alteration of one or more of the following: gene expression, gene function, cell proliferation, cell migration, apoptotic mechanisms, radiation response or drug response.

4. The method of claim 3, wherein the genetic material is a small interfering ribonucleic acid (siRNA).

5. The method of claim 2, wherein the therapeutic agent is a chemotherapeutic agent, and wherein the chemotherapeutic agent is temozolomide.

6. The method of claim 1, wherein the electric current or electric field is applied at about 0.1 milli-amps (mA) to about 4 amps (A).

7. The method of claim 1, wherein the electric current or electric field is applied at about 2 mA.

8. The method of claim 1, wherein the parameters are voltage of about +/−1-2 V at a frequency of 200 kHz.

9. The method of claim 1, wherein the parameters are voltage of about 4 V at a frequency of 130 Hz.

10. The method of claim 1, wherein the parameters include a frequency of more than 10 kHz.

11. The method of claim 1, wherein step (a) comprises implanting a single electrode in the site, and implanting an intratumoral electrode.

12. The method of claim 1, wherein step (a) comprises implanting multiple electrodes in the site.

13. The method of claim 1, wherein prior to step (a) the method comprises providing a device, the device including at least one electrode to deliver the electric current or electric field and one or more reference electrodes that are implanted in proximity to the at least one electrode that delivers the electric current or electric field.

14. The method of claim 1, wherein the site of the CNS suspected of having tumor cells includes a residual tumor bed in the CNS.

15. The method of claim 1, wherein the tumor in the CNS is a glioblastoma.

16. The method of claim 1, wherein one or more of the at least one electrode is insulated.

17. The method of claim 1, wherein the electric current or electric field has a frequency outside a range of neuronal entrainment.

18. The method of claim 1, wherein the electric current or electric field is alternating electric field.

19. The method of claim 1, wherein the electric current or electric field is alternating current.

20. The method of claim 1, wherein the parameters include voltage of about 1-10 V at frequency of 50 Hz to 500 kHz, or of voltage of about +/−1-10 V at frequency of 50 Hz to 500 kHz, or of voltage of about +/−1-10 V at frequency of 50-200 Hz.

21. An intratumoral modulation therapy (IMT) method for chronically reversing, minimizing, alleviating, or substantially inhibiting the progress or treatment resistance of a tumor in the central nervous system (CNS) in a patient in need, and preventing recurrence of the tumor in the CNS in the patient in need comprising:
    (a) chronically and surgically implanting in the patient in need at least one electrode that delivers electric current or electric field in a site, the site being selected from (i) a site adjacent to the tumor, (ii) a site within the tumor, or (iii) a site of the CNS suspected of having tumor cells, the at least one electrode having electrical leads connected thereto; and
    (b) generating the electric current or electric field having a combination of electrical parameters that preferentially targets neoplastic cells, and permanently and invasively applying to the site the electric current or electric field through the electrical leads to the electrode implanted in the site to provide permanently active therapy to the patient in need,
    wherein the electric current or electric field is alternating current or alternating electric field, and wherein the combination of electrical parameters includes a combination of voltages and frequencies that are suitable for permanently and invasively applying the electric current or electric field into the CNS of the patient in need.

22. An intratumoral modulation therapy (IMT) method for preventing recurrence of a tumor in the central nervous system (CNS) in a patient in need comprising:
    (a) chronically and surgically implanting in the patient in need at least one electrode that delivers electric current or electric field in a site, the site being a residual tumor bed in the CNS, the at least one electrode having electrical leads connected thereto; and
    (b) generating the electric current or electric field having a combination of electrical parameters that preferentially targets neoplastic cells, and permanently and invasively applying to the site the electric current or electric field through the electrical leads to the electrode implanted in the site to provide permanently active therapy to the patient in need, wherein the electric current or electric field is alternating current or alternating electric field, and wherein the combination of electrical parameters includes a combination of voltages and frequencies that are suitable for permanently and invasively applying the electric current or electric field into the CNS of the patient in need.

* * * * *